United States Patent
Odland et al.

(10) Patent No.: US 12,292,996 B2
(45) Date of Patent: *May 6, 2025

(54) MULTI-PARTY CONTROLLED TRANSIENT USER CREDENTIALING FOR INTERACTION WITH SECURE DATA

(71) Applicant: PLAYBACK HEALTH INC., New Hyde Park, NY (US)

(72) Inventors: Gregory Odland, Brooklyn, NY (US); Simerjot Singh, New Hyde Park, NY (US)

(73) Assignee: PLAYBACK HEALTH INC., New Hyde Park, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/340,319

(22) Filed: Jun. 23, 2023

(65) Prior Publication Data

US 2023/0401335 A1 Dec. 14, 2023

Related U.S. Application Data

(63) Continuation of application No. 17/806,446, filed on Jun. 10, 2022, now Pat. No. 11,727,145.

(51) Int. Cl.
*G06F 21/62* (2013.01)
*G06F 21/60* (2013.01)
(Continued)

(52) U.S. Cl.
CPC ........ *G06F 21/6245* (2013.01); *G06F 21/602* (2013.01); *G16H 10/60* (2018.01);
(Continued)

(58) Field of Classification Search
CPC ... G06F 21/6245; G06F 21/602; G16H 10/60; H04L 9/3228
See application file for complete search history.

(56) References Cited

U.S. PATENT DOCUMENTS 7,693,317 B2 4/2010 Vining et al.
7,805,377 B2 9/2010 Felsher
(Continued)

FOREIGN PATENT DOCUMENTS

CN 111261250 B 1/2021
CN 112650954 A 4/2021
(Continued)

OTHER PUBLICATIONS

A. Schellenbach, "New app gives ED patients aftercare instructions and med info," Hospital News, Oct. 31, 2016, accessed May 11, 2022, https://hospitalnews.com/patients-aftercare-instructions-technology/.

(Continued)

*Primary Examiner* — Oleg Korsak
(74) *Attorney, Agent, or Firm* — Thompson Patent Law Offices PC

(57) ABSTRACT

Apparatus and associated methods relate to provide transient access rights to entities for creating, accessing, and/or sharing digital health content (DHC). In an illustrative example, a health content distribution system (HCDS) may generate a time-limited access token (TLAT) for authenticated users to access DHC. The TLAT, for example, may be generated based on a predetermined association of a corresponding DHC with a patient, a predetermined association of a requestor with the patient, a predetermined role of the requestor with relation to the patient, and a predetermined association between the requestor and a creator of the content. The TLAT may be further generated based on a predetermined association between the requestor and an organization associated with the patient. The HCDS may, for example, upon receiving the TLAT, transmit the corresponding DHC to be displayed at the requestor's device. Various (Continued)

embodiments may advantageously provide a secure on-demand health content access system.

20 Claims, 18 Drawing Sheets

(51) Int. Cl.
　　*G16H 10/60*　　　(2018.01)
　　*H04L 9/32*　　　　(2006.01)
(52) U.S. Cl.
　　CPC .... *H04L 9/3228* (2013.01); *G06F 2221/2137* (2013.01); *G06F 2221/2141* (2013.01)

(56) References Cited

U.S. PATENT DOCUMENTS

| | | | |
|---|---|---|---|
| 8,316,237 | B1 | 11/2012 | Felsher et al. |
| 8,843,852 | B2 | 9/2014 | Berry et al. |
| 9,058,635 | B1 | 6/2015 | Rybkin |
| 9,107,586 | B2 | 8/2015 | Tran |
| 9,286,442 | B2 | 3/2016 | Csoma et al. |
| 10,528,702 | B2 | 1/2020 | Cox et al. |
| 10,546,148 | B1 | 1/2020 | Stolboushkin |
| 11,727,145 | B1* | 8/2023 | Odland ............... G06F 21/6245 726/28 |
| 2005/0147284 | A1 | 7/2005 | Vining et al. |
| 2008/0013705 | A1 | 1/2008 | Yoffie et al. |
| 2009/0125332 | A1 | 5/2009 | Martin |
| 2010/0223073 | A1 | 9/2010 | Nearman et al. |
| 2010/0262435 | A1 | 10/2010 | Smith et al. |
| 2012/0159391 | A1 | 6/2012 | Berry et al. |
| 2013/0085771 | A1 | 4/2013 | Ghanbari et al. |
| 2014/0136235 | A1 | 5/2014 | Lee |
| 2014/0313303 | A1 | 10/2014 | Davis et al. |
| 2014/0324462 | A1 | 10/2014 | Beck et al. |
| 2014/0359085 | A1 | 12/2014 | Chen |
| 2015/0077502 | A1 | 3/2015 | Jordan et al. |
| 2015/0264015 | A1 | 9/2015 | Cialdea et al. |
| 2015/0331997 | A1 | 11/2015 | Joao |
| 2016/0117448 | A1 | 4/2016 | Craen et al. |
| 2017/0068785 | A1 | 3/2017 | Experton et al. |
| 2017/0116384 | A1 | 4/2017 | Ghani |
| 2018/0191735 | A1 | 7/2018 | Lahoz et al. |
| 2018/0253840 | A1 | 9/2018 | Tran |
| 2018/0276341 | A1 | 9/2018 | Rab et al. |
| 2019/0005251 | A1 | 1/2019 | Hamlin et al. |
| 2019/0043040 | A1 | 2/2019 | Malmborg et al. |
| 2020/0052896 | A1 | 2/2020 | Acharya et al. |
| 2020/0066401 | A1 | 2/2020 | Guelich et al. |
| 2020/0084037 | A1 | 3/2020 | Zhang et al. |
| 2020/0168306 | A1 | 5/2020 | Chen et al. |
| 2020/0302037 | A1 | 9/2020 | Kawamura |
| 2020/0365258 | A1 | 11/2020 | Langer et al. |
| 2021/0110060 | A1 | 4/2021 | Sacks |
| 2021/0144010 | A1 | 5/2021 | Tang et al. |
| 2021/0150051 | A1 | 5/2021 | Noordende |

FOREIGN PATENT DOCUMENTS

| | | |
|---|---|---|
| CN | 113127825 A | 7/2021 |
| KR | 20180076911 A | 7/2018 |
| WO | 2020236678 A1 | 11/2020 |

OTHER PUBLICATIONS

Broeckelmann, OAuth 2 Access Token Usage Strategies for Multiple Resources (APIs), Part 1, Arp 18, 2019, 12 pages.
Canvas Solutions Inc, "Discharge Instructions for Healthcare Professionals," GoCanvas, accessed May 11, 2022, https://www.gocanvas.com/mobile-forms-apps/10151-Discharge-Instructions-for-Healthcare-Professionals.
Carequality, FHIR-Based Exchange Implementation Guide, Version 1.0, Dec. 1, 2020, 67 pages.
Coremobile, e-Discharge Management Solution, retrieved from the internet May 16, 2022, https://www coremobileinc.com/eDischarge_Management_Solutioncm. php.
E. Olsen, "Laguna Health launches new tool to help patients after hospital discharge," MobiHealthNews, Sep. 8, 2021, accessed May 11, 2022, https://www.mobihealthnews.com/news/laguna-health-launches-new-tool-help-patients-post-hospital-discharge.
International Search Report and Written Opinion of the International Searching Authority in related International Application No. PCT/US2022/072888, dated Feb. 20, 2023, 15 pages.
Jacobs, et al, How to deliver better discharge support to patients by utilizing mobile, social media and other technologies, Dell, 40 pages.
Leventhal, R, Discharged With a Recording: How Cullman Regional is Optimizing Readmissions Work, Healthcare Innovation, Oct. 3, 2013, retrieved from the internet, https://www.hcinnovationgroup.com/population-health-management/mobile-health-mhealth/article/13022093/discharged-with-a-recording-how-cullman-regional-is-optimizing-readmissions-work.
Maguire, P, Want to cut readmissions? Try hitting "record", Today's Hospitalist, Jul. 2014, retrieved from the internet, https://www.todayshospitalist.com/want-to-cut-readmissions-try-hitting-record/.
PatientEngagementHIT, "Tracking Patient Satisfaction Key to a Consumer-Driven Strategy," PatientEngagementHIT, Oct. 4, 2021, accessed Nov. 2, 2021, https://patientengagementhit.com/news/tracking-patient-satisfaction-key-to-a-consumer-driven-strategy.
Relias Media, Forms guide individualized discharge instruction, May 1, 2000, retrieved from the internet, https://www.reliasmedia.com/articles/61738-forms-guide-individualized-discharge-instruction.
Vocera, "Discharge Communication," Vocera, accessed May 11, 2022, https://www.vocera.com/product/vocera-care-inform.
Vocera, Digital Patient Discharge Process Recognized as 'Always Event' by IHI, GlobeNewswire, Feb. 4, 2014, retrieved from the internet, https://finance.yahoo.com/news/digital-patient-discharge-process-recognized-235701786.html.
Vocera, Good To Go Solution, Culman Regional Medical Center, 2014, 2 pages.
Vocera, Vocera Care Experience, 2019, 4 pages.
Wasabi Technologies, "How do I generate pre-signed URLs for temporary access with Wasabi?," Wasabi Knowledge Base, accessed Dec. 7, 2021, https://wasabi-support.zendesk.com/hc/en-us/articles/360022853592-How-do-I-generate-pre-signed-URLs-for-temporary-access-with-Wasabi-.
Chapter II Demand filed in related International Application No. PCT/US2022/072888, dated Apr. 9, 2024, 32 pages.
Notice of Informal Communications in related International Application No. PCT/US2022/072888, dated Jul. 3, 2024, 3 pages.
Written Opinion of the International Preliminary Examining Authority in related International Application No. PCT/US2022/072888, dated May 3, 2024, 5 pages.

* cited by examiner

MULTI-PARTY CONTROLLED TRANSIENT USER CREDENTIALING FOR INTERACTION WITH SECURE DATA

CROSS-REFERENCE TO RELATED APPLICATIONS

This application is a Continuation of and claims the benefit of U.S. application Ser. No. 17/806,446, titled "Multi-party Controlled Transient User Credentialing for Interaction with Patient Health Data," filed by Gregory Odland, et al., on Jun. 10, 2022.

This application incorporates the entire contents of the foregoing application(s) herein by reference.

The subject matter of this application may have common inventorship with and/or may be related to the subject matter of the following:

U.S. Application Ser. No. 62/849,716, titled "PATIENT COMMUNICATION AND NOTIFICATION SYSTEM WITH PROVIDER AND PATIENT MULTIPLY SOURCED AND UPDATED DATABASES AND INFORMATION COMMUNICATIONS BACKBONE," filed by David Langer, et al., on May 17, 2019;

U.S. Application Ser. No. 62/947,544, titled "HEALTHCARE PROVIDER AND PATIENT COMMUNICATIONS SYSTEM," filed by David Langer, et al., on Dec. 13, 2019;

U.S. application Ser. No. 16/876,083, titled "APPARATUS FOR GENERATING AND TRANSMITTING ANNOTATED VIDEO SEQUENCES IN RESPONSE TO MANUAL AND IMAGE INPUT DEVICES," filed by David Langer, et al., on May 17, 2020; and, PCT Application Serial No. PCT/US2020/033328, titled "APPARATUS FOR GENERATING AND TRANSMITTING ANNOTATED VIDEO SEQUENCES IN RESPONSE TO MANUAL AND IMAGE INPUT DEVICES," filed by David Langer, et al., on May 17, 2020.

This application incorporates the entire contents of the foregoing application(s) herein by reference.

TECHNICAL FIELD

Various embodiments relate generally to digitally store, distribute, and authenticate health related content.

BACKGROUND

Health professionals often perform their analysis and devise healthcare recommendations at least partially based upon health records of patients. Health records, including medical history, observations, previously administrated drugs and therapies, lab test results, X-rays and other images, and/or other medical reports from previous examinations, may be useful at different times for treating a patient. It may, for example, be desirable to maintain complete and accurate medical records.

An electronic health record (EHR) is a collection of patient and population electronically stored health information in a digital format. For example, EHRs may include a patient's demographics, medical history, medication and allergies observations, immunization status, previous laboratory test results, radiology images, vital signs, personal statistics like age and weight, and billing information.

In some cases, EHRs may be used to improve healthcare quality. For example, some EHRs may combine a large number of patients demographics. These data may be, for example, used to identify demographically similar patient and/or help clinicians to identify and stratify chronically ill patients. Sometimes, EHR can improve quality care by using the data and analytics to prevent hospitalizations among high-risk patients.

SUMMARY

Apparatus and associated methods relate to providing transient access rights to entities for creating, accessing, and/or sharing digital health content (DHC). In an illustrative example, a health content distribution system (HCDS) may generate a time-limited access token (TLAT) for authenticated users to access DHC. The TLAT, for example, may be generated based on a predetermined association of a corresponding DHC with a patient, a predetermined association of a requestor with the patient, a predetermined role of the requestor with relation to the patient, and a predetermined association between the requestor and a creator of the content. The TLAT may be further generated based on a predetermined association between the requestor and an organization associated with the patient. The HCDS may, for example, upon receiving the TLAT, transmit the corresponding DHC to be displayed at the requestor's device. Various embodiments may advantageously provide a secure on-demand health content access system.

Various embodiments may achieve one or more advantages. For example, some embodiments may include a two-factor authentication to advantageously provide an extra layer of security for the patient's DHC. For example, some embodiments may include generating a human-readable indicium for the TLAT to advantageously improve usability of the HCDS. Some embodiments may, for example, include operations to generate a time-limited creation token to provide transient content creation rights to the requestor to advantageously protect the patient to receive only content from authenticated users. For example, some embodiments may include communication modules to communicate with medical devices to advantageously automatically save and associate results with the patients at the HCDS. Some embodiments, for example, may provide a patient referral method for advantageously providing instant access to the patient's record upon connection completion.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

To aid understanding, this document is organized as follows. First, to help introduce discussion of various embodiments, a Health Content Distribution Platform (HCDP) is introduced with reference to FIGS. 1-2. Second, that introduction leads into a description with reference to FIGS. 3-7 of some exemplary embodiments and graphical user interfaces of the HCDP. Third, with reference to FIGS. 8-12, this document describes exemplary apparatus and methods useful for storing, distributing, sharing, and sending digital health content. Finally, the document discusses further embodiments, exemplary applications and aspects relating to securely and instantly distribution of on-demand health related content.

Figure 1:
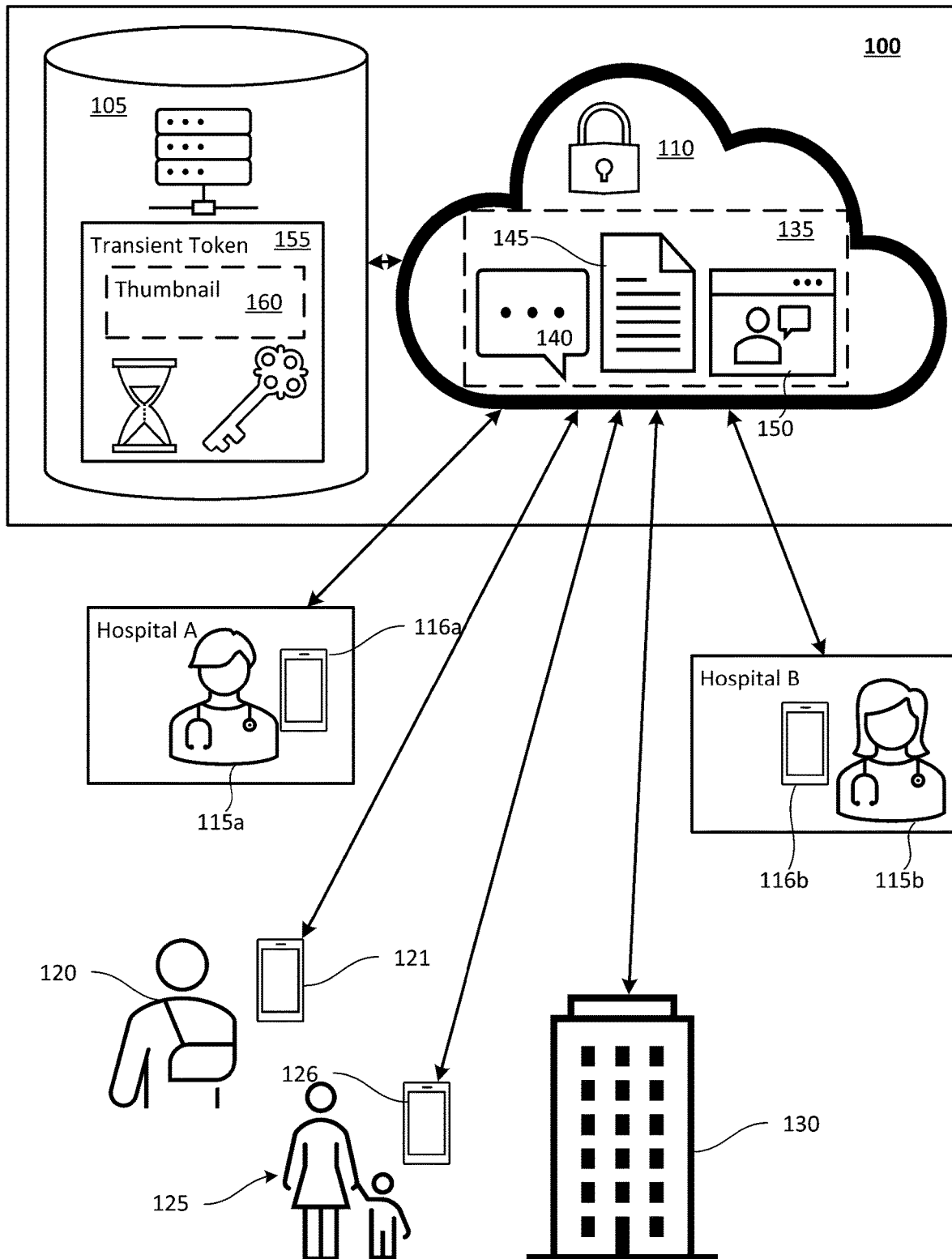
FIG. 1 depicts an exemplary Health Content Distribution Platform (HCDP) employed in an illustrative use-case scenario.

FIG. 1 depicts an exemplary Health Content Distribution Platform (HCDP) 100 employed in an illustrative use-case scenario. For example, the HCDP 100 may provide secured and credential-validated access to electronic health records. For example, the electronic health records may be associated with a patient, a healthcare professional, a healthcare related enterprise, and/or a combination thereof. The HCDP 100 includes a content authorization server (CAS 105) and a secure cloud storage (SCS 110). The CAS 105, for example, may authenticate a user's request for accessing health data. For example, the user may be a healthcare professional or a patient using the HCDP 100. In some implementations, the user may include other authorized individuals (e.g., government agents) who are authorized to access to the electronic health records. For example, the SCS 110 may be a cloud storage capable of storing and transmitting digital content. In some implementations, the SCS 110 may be a secured private cloud storage accessible only by authenticated users of the HCDP 100. In various implementations, the CAS 105 and the SCS 110 may be operably connected (e.g., via the Internet and/or via a private network) to process user's requests.

The SCS 110, as shown, communicates with various users and entities. As an illustrative example, physicians 115a, 115b, a patient 120, the patient's family members 125, and other health entities 130 is communicating with the SCS 110 using their mobile devices. As shown, the physician 115a is using a device 116a (e.g., mobile device, smartphone, wearable, desktop, laptop, computing system, medical device) to access the SCS 110, the physician 115b is using a device 116b (e.g., mobile device, smartphone, wearable, desktop, laptop, computing system, medical device) to access the SCS 110, the patient 120 is using a device 121 (e.g., mobile device, smartphone, wearable, desktop, laptop, computing system, medical device) to access the SCS 110, and the family members 125 are using devices 126 (e.g., mobile device, smartphone, wearable, desktop, laptop, computing system, medical device) to access the SCS 110. In some implementations, various users may access the SCS 110 to advantageously create and share digital health content with other users within or outside of the HCDP 100.

As an illustrative example, after a visit from the patient 120, the physician 115a may create a digital health content (DHC), in a form of a video message, such as related to care techniques and treatments of a broken arm of the patient 120. In some examples, the patient 120 and the family members 125 may be authorized to review the video message by accessing the SCS 110, using their devices 121, 126. For example, the patient 120 may access the SCS 110 using a mobile application installed in the device 121. By storing DHCs in the SCS 110 and providing access to the patient 120 and the family members 125, in some implementations, the patient 120 and the family members 125 may, for example, instantly review (e.g., re-review) the DHCs on-demand. Accordingly, the HCDP 100 may advantageously reduce loss of care information useful for the patient 120.

The physician 115a may, in some implementations, connect another physician 115b of another hospital to selectively view some or all DHCs of the patient 120. For example, the physician 115a may authorize the physician 115b to view and comment on X-ray images of the patient 120. In some examples, the HCDP 100 may allow sharing of key results of the patient 120. For example, the HCDP 100 may advantageously reduce duplicate lab tests and costs across different clinics and/or healthcare entities.

In this example, the SCS 110 may also authenticate the other health entities 130 for access. For example, the other health entities 130 may include health insurance companies. For example, the other health entities 130 may include external healthcare provides including laboratories providing health services. In some implementations, the other health entities 130 may include government agencies (e.g., Medicare, Center for Disease Control). In some implementations, the external health entities 130 may include external health record systems interfacing with the HCDP 100. In some implementations, the other health entities 130 may, by way of example and not limitation, include medical device companies. The other health entities 130 may, for example, include hospitals and/or health systems. The other health entities 130 may, for example, include wearables (e.g., cloud systems, apps, wearable devices such as fitness trackers). The other health entities 130 may, for example, include pharmacies and/or other pharma entities. The other health entities 130 may, for example, include payors. The other health entities 130 may, for example, include other stakeholder(s) in a patient's care. Various health entities 130 may be selectively authorized, for example, to view and/or create selected DHCs based on a role or capacity of the entity 130, for example.

The SCS 110, in this example, stores various DHCs 135 including a text message 140, an electronic health record 145, and a video content 150. In various implementations, other content may also be available. For example, the DHC 135 may also include voice messages, health tips associated to the patient 120 (e.g., exercise for recovering from a broken arm), schedule of next appointments at various clinics, information of prescribed medications, instant message contact list to related care providers, and/or other health related content associated with the patient 120. In some implementations, the DHCs 135 may be stored in an encrypted format. For example, the SCS 110 may use AES256 encryption standard for storing the DHCs 135.

In some implementations, the HCDP 100 may selectively credential users (e.g., the physicians 115*a*, 115*b*, the patient 120, the family members 125, and other health entities 130) with read and/or write access to the DHCs 135 using time-limited access tokens. In this example, when an access request of one of the DHCs 135 is received from one of the users, the CAS 105 authenticates and generates a time-limited token 155 for authorizing time-transient access to the requested DHC 135. In some implementations, the time-limited access token 155 may, for example, be generated based on an intersection between at least: (1) a predetermined association of a requestor with the patient 120, (2) a predetermined role of the requestor with relation to the patient 120 (e.g., friend, family, physician), and (3) a predetermined association between the requestor and a creator of the DHC 135 (e.g., member of the same medical institution who generated the DHC 135). For example, the access granted and/or records (e.g., media) associated with the tokens may be dynamically generated by the CAS 105 based on the predetermined role(s) and/or associations.

In some implementations, the time-limited access token 155 may, for example, be presented as individual resource locators (e.g., uniform resource identifiers (URIs)) having the time-limited access token 155 embedded. In response to a request from an authorized user (e.g., the family members 125 of the patient 120) for one of the DHCs 135, the authorized user may be, in some examples, presented with a list of the time-limited access tokens 155. For example, each of the time-limited access tokens 155 may be associated with at least one specific (e.g., individual piece of) DHC 135 (e.g., the text message 140, the electronic health record 145, or the video content 150) associated with the patient 120. For example, the CAS 105 may select and generate the time-limited access tokens 155 based on the authorized user's role with respect to the patient 120. In some examples, the CAS 105 may select and generate the time-limited access tokens 155 based on the authorized user's role with respect to a creator of each of the DHCs 135.

In some implementations, the list of time-limited access tokens 155 may, for example, be presented using human-readable indicia. The token 155, in this example, includes a thumbnail 160. For example, the thumbnail 160 may be a thumbnail of an image DHC. In some examples, the thumbnail 160 may be a frame of a video DHC (e.g., selected by a creator of the video DHC, automatically selected using an artificial intelligence selection program, or using other selection method). In some examples, the thumbnail 160 may be an icon associated with the corresponding content (e.g., a text message icon representing a text message DHC). In various implementations, the thumbnail 160 may include an embedded link to access an associated DHC. Accordingly, for example, an authenticated user may advantageously select from a human readable list of visual indicium, one or more DHCs to be displayed.

Various embodiments may, for example, advantageously provide a technical solution to the problem of granting transient access to digital media associated with patient health records across diverse stakeholders. For example, a person needing only temporary access to paper health records may be physically shown the records by an entity (e.g., a hospital) that created and is responsible for the records. The responsible entity may, for example, be able to physically retain control and ensure security of the records. For example, if a doctor needs to see the records, he may be granted physical access (e.g., check-out), and then be required to return the records (e.g., check-in) within a period of time. Physical absence of the records may, for example, provide accountability by prompting a responsible entity to follow-up with the last person who checked out the records.

However, in a digital environment, providing temporary access can be very difficult, particularly in the face of confidentiality and/or privacy regulations (e.g., regulations associated with the Health Insurance Portability and Accountability Act, also known as HIPAA) and policies (e.g., insurance requirements). Many existing electronic medical records (also known as "EMRs" and/or electronic health records or "EHRs") seek to ensure security and/or privacy by draconian firewalls and/or 'siloed' data. For example, sharing data between hospitals may be extremely difficult, and sharing between EHRs may be nearly impossible. Methods to allow for transfer or sharing of medical records is often complex, usually completed by a lengthy and cumbersome sign-off process that requires in-person authentication, paper printouts, and faxing Many personnel may end up resorting to operating in an ethically and/or legally 'gray area' in order to take advantage of the everyday technology they rely on (e.g., smartphones with portable cameras and microphone, text messaging, video messaging) to communicate in a busy setting. For example, emergency responders may use multi-media messaging via their smartphone to rapidly convey lifesaving information to smartphones of emergency room physicians about an incoming patient. Referring doctors may, for example, snap a photo of lab results (e.g., on a display connected to a siloed EMR!) or send a video message over unsecured MMS to referral physicians to rapidly bring the referral physician up to speed on a case. The information may, for example, simply live in the various smartphones, with little thought for HIPAA requirements or data privacy in the bustle of the emergency room. The information may, for example, be difficult to link to a traditional EMR. Accordingly, valuable information may be lost and/or sensitive data may be vulnerable to hacking, accidents (e.g., selling the phone, losing the phone), and/or theft. Patients may have little way to access the data, let alone share it with other persons (e.g., family, primary care physicians) in any organized way, if at all.

In various implementations, the HCDP 100 may, for example, advantageously provide a technological solution to a technical problem arising from a necessity of communication of medical records over a plethora of distributed, uncontrolled devices (e.g., smartphones, laptops, tablets), while maintaining security and privacy of sensitive patient health data. Various embodiments may advantageously break down digital barriers and provide a technological solution to a technical problem of enabling rapid and easy (e.g., 'natural') communication in the flow of daily life between the distributed, uncontrolled devices of various stakeholders (e.g., patients, physicians, family members, insurance companies) while still maintaining the integrity and future accessibility of the various health-record-related content being generated and/or shared.

For example, implementations having a transient token-based access to medical records, the tokens being dynamically generated for each piece of content based on a threefold requestor role with respect to a patient, requestor and patient association, and requestor and content creator association, may advantageously provide a technical solution to the problem of sharing and/or creating digital health records between distributed devices outside of a siloed, firewalled EMR network. Generating displays of available content and streaming the requested content in response to the tokens generated (in response to, for example, at least the intersection of the threefold roles/permissions) may advantageously, for example, provide a technical solution to the technical problem of preserving privacy while allowing distributed digital access to create and/or access patient health records to and from the myriad devices relied on in today's medical industry and society at large.

For example, such implementations may advantageously enable temporary access to (e.g., to create and/or access digital health record objects) a secure health record environment using methods and/or data structures unknown and unneeded in the world of paper records. For example, transient access to create and/or access digital content in a health record system may be granted—and even only become visible to requestor—based on token(s) dynamically generated based on ordered, predetermined sets of rules designed to solve problems arising in the context of distributed electronic devices sharing, creating, and/or accessing sensitive medical records.

Figure 2:
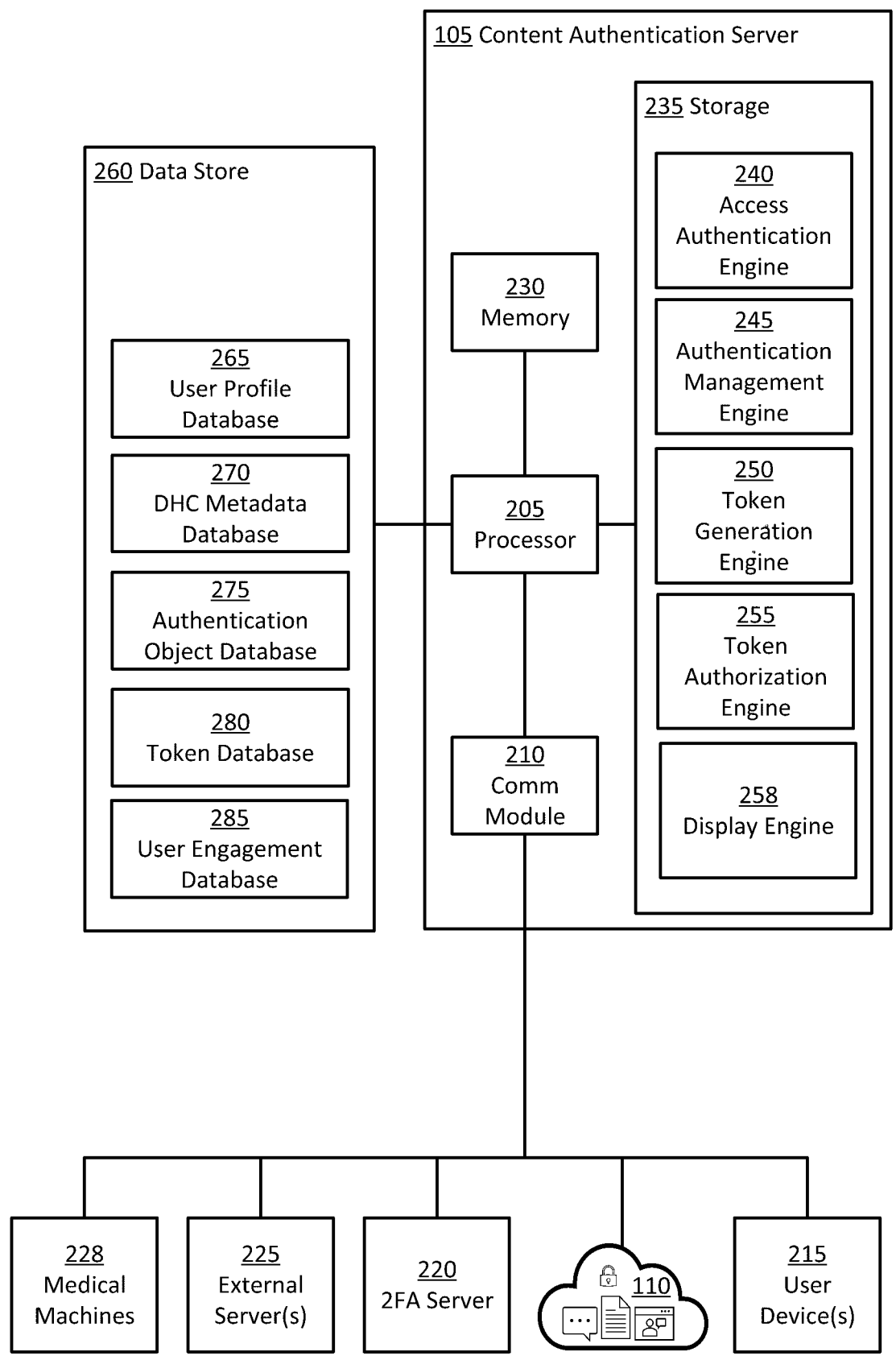
FIG. 2 is a block diagram depicting an exemplary communication authentication server (CAS).

FIG. 2 is a block diagram depicting an exemplary communication authentication server (CAS) 105. The CAS 105 includes a processor 205. The processor 205 may, for example, include one or more processor. The processor 205 is operably coupled to a communication module 210. The communication module 210 may, for example, include wired communication. The communication module 210 may, for example, include wireless communication. In the depicted example, the communication module 210 is operably coupled to at least one user devices 215. For example, the user devices 215 may include mobile devices of users and/or desktop computer of users. In the depicted example, the communication module 210 is operably coupled to the SCS 110. The communication module 210 is operably coupled to one or more two factor authorization (2FA) server 220. For example, the CAS 105 may activate the 2FA server 220 to authenticate a request from one of the user devices 215. For example, the communication module 210 is operably coupled to external servers 225. For example, the external server 225 may include a Health Level Seven International (HL7) Fast Healthcare Interoperability Resources (FHIR) interface that may supply data feed to the HCDP 100. For example, the external server 225 may include, Google Cloud Service, Amazon Web Services, and/or other analytical/data services connecting through an Application Programming Interface (API).

In this example, the communication module 210 is operably coupled to one or more medical devices 228. For example, the medical devices 228 may be an X-ray machine. In some implementations, the medical devices 228 may be authenticated to store medical data associated with a patient into the SCS 110. As an illustrative example, the X-ray machine may be authorized to save a copy of digital X-ray images of a patient to the SCS 110 after the images have been taken.

The processor 205 is operably coupled to a memory module 230. The memory module 230 may, for example, include one or more memory modules (e.g., random-access memory (RAM)). The processor 205 includes a storage module 235. The storage module 235 may, for example, include one or more storage modules (e.g., non-volatile memory). In the depicted example, the storage module 235 includes an access authentication engine (AAE) 240, an authentication management engine (RME) 245, a token generation engine (TGE) 250, and a token authorization engine (TAE) 255, and a display engine 258. The processor 205 further operably coupled to a data store 260. The data store, as depicted, includes a user profile database 265, a DHC metadata database 270, an authentication object database 275, a token database 280, and a user engagement database 285.

The AAE 240 may, for example, authenticate read and write access requests received from the user devices 215. In some implementations, the AAE 240 may authenticate an access request of a DHC associated with a patient from a requestor by comparing, based on information stored in the user profile database 265 and the authentication object database 275, an association between the requestor and the patient and an association between a role of the requestor and the patient. For example, the AAE 240 may retrieve an identity and a role of the requestor from the user profile database 265. Based on the identity and the role, the AAE 240 may compare the identity and the role with a patient relation object retrieved from the authentication object database 275. In some implementations, the AAE 240 may authenticate an access request of a DHC by comparing an association between the requestor and a creator of the DHC based on the DHC metadata database 270 and the user profile database 265. For example, a laboratory technician may create a lab result DHC to be stored in the SCS 110. In some examples, the DHC metadata database 270 may include metadata of the lab result DHC is a result of a test initiated by a physician X. For example, the physician X may be associated in the metadata of the lab result DHC so that the physician X may be granted view access.

The AME 245 may, for example, manage authentications of DHCs between a patient and other health care entities. In some implementations, the AME 245 may generate a predetermined patient access rules based on a patient selected preference. In some implementations, a patient may add physicians, family members, or other health care entities into a support team. For example, the AME 245 may define that those members of the support team may receive at least read access to at least some DHCs associated with the patient. In some implementations, a healthcare enterprise (e.g., a hospital) may, for example, use the AME 245 to define a role of a healthcare profession. For example, the health care enterprise may assign a role of doctors, nurse, lab technicians to each of the users within the health care enterprise. In some implementations, the AME 245 may selectively assign authentication rules based on the role of each of the healthcare profession assigned by the healthcare enterprise. In some implementations, users with existing authentication access may use the AME 245 to selectively share access of selected records with other users.

In some implementations, the AME 245 may generate an authentication object based on a pre-existing medical relationship of the patient. For example, when a patient visited a physician at a hospital, the physician may be automatically added to the patient's care team. For example, support staff (e.g., nurses) in the same hospital may, for example, automatically be permitted access to the patient's records. The access may be limited, for example, by predetermined hospital access rules, role of the staff member, and/or the predetermined patient access rules. In some implementations, a creator of a DHC may use the AME 245 to create connection of a DHC to other healthcare providers. For example, a lab technician may use the AME 245 to connect a physician to a particular lab result DHC using the AME 245. In various implementations, the AAE 240 may use relations between a patient and a requestor, including a role of a requestor, an organization of the requestor, and a relation between the requestor and a creator of each of the DHC related to the patient, defined by the AME 245 to determine whether the requestor has a right to access to read and/or write the DHC. Accordingly, access to the DHCs may advantageously be simultaneously managed by the healthcare providers, the healthcare professions, and the patients.

After an access to a DHC is determined, the TGE 250 may generate a time-limited access token to the DHC. In some implementations, the generated time-limited access token may be stored in the token database 280. In some implementations, the TGE 250 may also generate a time-limited creation token providing access to associate digital content from the requestor with the patient. For example, the time-limited creation token may be generated based on a predetermined association of a creation requestor with a patient and a predetermined role of the requestor with relation to the patient. For example, the authentication object database 275 may identify that a physician is a family doctor of a patient. In some examples, the family doctor may receive the time-limited creation token when the family doctor request to send a DHC (e.g., a text message reminding of a regular checkup visit) to the patient.

In some implementations, the time-limited tokens may be generated based on a predetermined association between a requestor and an organization associated with a patient. For example, after the patient visited a clinic, the TGE 250 may generate a time-limited creation token to physicians and nurses of the clinic so that they can send text messages and videos to the patient after the visit.

The TAE 255, for example, may validate a received time-limited access token from the user device 215. For example, the TAE 255 may validate the received time-limited access token by comparing the received token with a saved copy in the token database. In some implementations, the TAE 255 may use the 2FA server 220 to validate an identity of a send of the received time-limited access token.

After the received time-limited access token is validated, for example, the display engine 258 may access the SCS 110 to retrieve an associated DHC for display. In some implementations, the display engine 258 may display the associated DHC online (e.g., by streaming) without transmitting full content of the DHC to the user devices 215. Accordingly, for example, the display engine 258 may display the DHC via the Internet securely.

The user engagement database 285 may store usage information of patients, content providers, and other health entities of the HCDP 100. For example, the CAS 105 may use the user engagement database 285 to generate flexible dashboards to follow platform use by providers, patients, and family members. In some examples, a system administrator may review responses from patients to a content creator. For example, the system administrator may provide relevant training to the content creator based on the reviewed responses.

Figure 3:
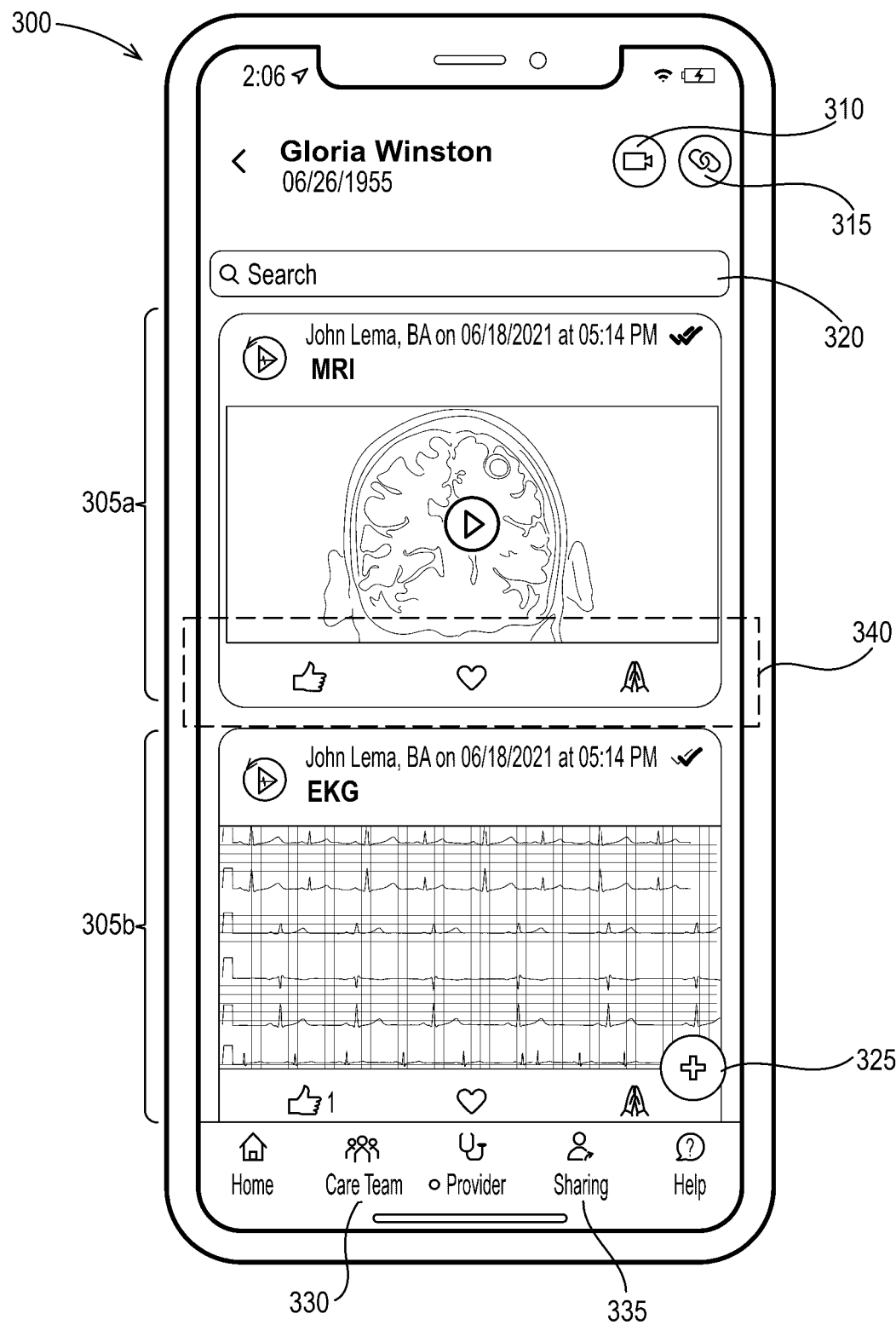
FIG. 3 depicts an exemplary user interface of the HCDP on a user mobile device.

FIG. 3 depicts an exemplary user interface (UI) 300 of a mobile application for accessing the HCDP 100 on a user mobile device (e.g., the devices 116a, 116b). In this example, the UI 300 is displaying DHCs 305a, 305b of a patient "Gloria Winston." The UI 300 includes a video call button 310 and a connect button 315. In some implementations, upon selecting the video call button 310, the mobile application may call the patient for a video conference. In some implementations, the connect button 315 may connect the patient with other health providers. For example, upon successful connection, the connected health provider may gain access to at least some of the DHC of the patient. An illustrative connecting example are described with reference to FIG. 6. The UI 300 includes a search bar 320. For example, a user may use the search bar 320 to search available DHC (e.g., currently have view access associated with the user) associated with the patient.

In this example, the UI 300 includes a creation button 325. For example, a health provider may use the creation button to create a DHC for the patient. Upon the DHC is created and saved in the SCS 110, the HCDP 100 may notify the patient to view the created DHC, for example.

The UI 300 further includes a care team button 330. For example, upon selecting the care team button 330, the UI 300 may display a list of members within a care team. In some examples, the care team may be defined by the patient. In some examples, the care team may be automatically populated by rules defined by an enterprise associated with the patient. For example, the enterprise may populate doctors, nurses, and other supporting members related to the patient's healthcare to the care team. The UI 300 includes a share button 335 to share selected DHCs. In some examples, the share button 335 may be used to share selected DHCs via external communication channels. For example, the HCDP 100 may send a link to the selected DHC via email, text messages, or other mobile messaging applications.

For each of the displayed DHCs 305a, 305b, the UI 300 includes an emoticon bar 340. In some implementations, a viewer of the displayed DHCs 305a, 305b may engage with selecting an emoticon (e.g., "like", "love", "thanks" in the depicted example) displayed in the emoticon bar 340. In various implementations, the engagement received from viewers associated with the DHCs may be saved and reviewed. For example, the engagement received may be stored in the user engagement database 285.

In an illustrative example without limitation, when a user opens the mobile application, the HCDP 100 may identify a role of the user. For example, if the user is a patient, the mobile application may display a list of DHC associated with the patient. For example, if the user is a health provider, the mobile application may display a list of patients currently associated with the user. As an illustrative example, the user may select one of the patients in the list. The mobile applications, for example, may send a request to the HCDP 100 to retrieve DHCs related to the selected patient accessible to the user. Upon authentication, the mobile application may receive a list of time-limited access tokens associated with the accessible DHCs (e.g., the DHCs 305a, 305b). In some implementations, each of the received time-limited access tokens may be rendered in the UI 300. For example, as the user scroll through the DHCs on the UI 300, the mobile application may, in some implementations, call an API for a thumbnail associated with the DHC. When the user clicks on a thumbnail, an embedded link to the DHC is retrieved so that the DHC is played back. In various implementations, the time-limited access tokens (and the link embedded in the token) may expire after a predetermined time. Accordingly, the time-limited access tokens may advantageously prevent unauthenticated access to the DHC using an expired token or an expired link.

In some implementations, the mobile application may provide a role-specific display. As shown, the UI 300 may be a provider specific display. For example, the mobile app may be configured that the UI 300 may display medical comments that are available to medical doctors only. For example, the patient may see, on the mobile application, the DHC associated to the medical comment but not the medical comment itself.

Figure 4:
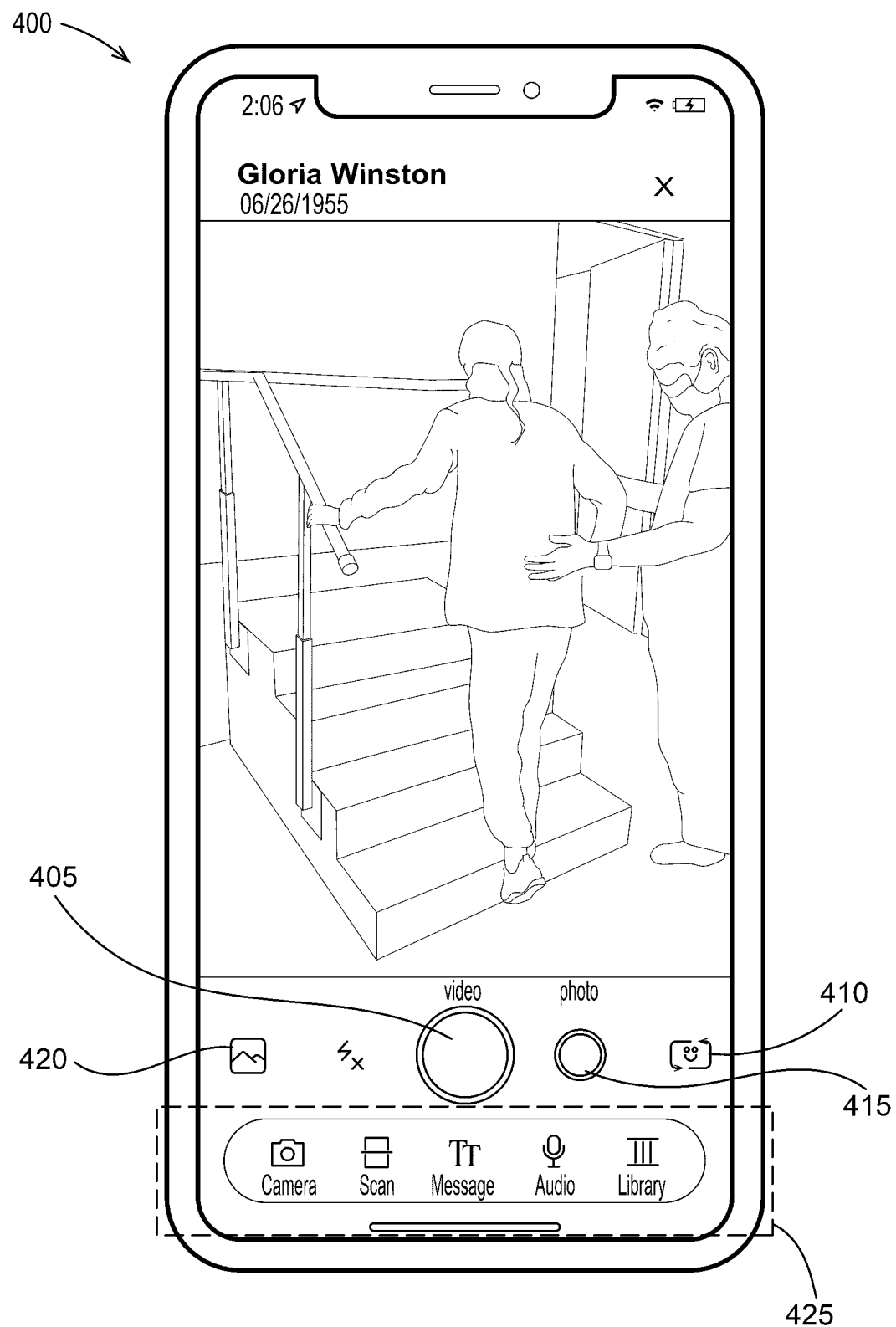
FIG. 4 depicts an exemplary user interface for creating digital health content (DCH) for the HCDP.

FIG. 4 depicts an exemplary user interface (UI 400) for creating the digital health content (DCH) 135 for the HCDP 100. For example, the UI 400 may be displayed when a user selects the create content button 325 of the mobile application as described with reference to FIG. 3. In this example, the user is using the UI 400 to create a video DHC for a patient "Gloria Winston." For example, the user may have a predetermined association with the patient. In various implementations, the user may request a write access to the patient's health records. In some implementations, the CAS 105 may, for example, generating a time-limited creation token providing access to associate DHC from the user with the patient. For example, the CAS 105 may generate the time-limited creation token generated based on a predetermined association between the user and the patient, a predetermined role of the user with relation to the patient, and/or an association between the patient and an enterprise associated with the user. In this example, the user may be a physician verified (e.g., in the authentication object database 275) to create content for the patient.

As shown in this example, the user may press a video button 405 to start capturing a video. The UI 400 also includes a camera flip button 410 to toggle video capture device between a front view camera and a rear view camera. For example, the user may use the front view camera to record personal video message. The UI 400 also includes a photo shutter button 415. For example, instead of taking a video, the user may use the photo shutter button 415 to capture an image photo. In some examples, the user may also use video or image stored in the mobile device to send to the patient by selecting a gallery button 420.

Although an example of creating content with camera is shown in FIG. 4, other modes of content creation may be available. In this example, the UI 400 include a mode selection bar 425. By selecting different mode in the mode selection bar 425, the user may choose to create a DHC by using a camera, scanning a document, typing a text message, recording an audio, and retrieve from a library of content. For example, the library of content may include previously created caring procedures, health tips, exercise video, test preparation procedures, and/or other health related information.

Although an illustrative example of sending DHC from a health provider to a patient is described, other transmission direction may be possible. For example, a patient may create DHCs to be sent to an associated clinic for examination. For example, for quick medical assessment, the patient may send a photo of a wound to a family doctor previously defined in the authentication object database 275.

Figure 5:
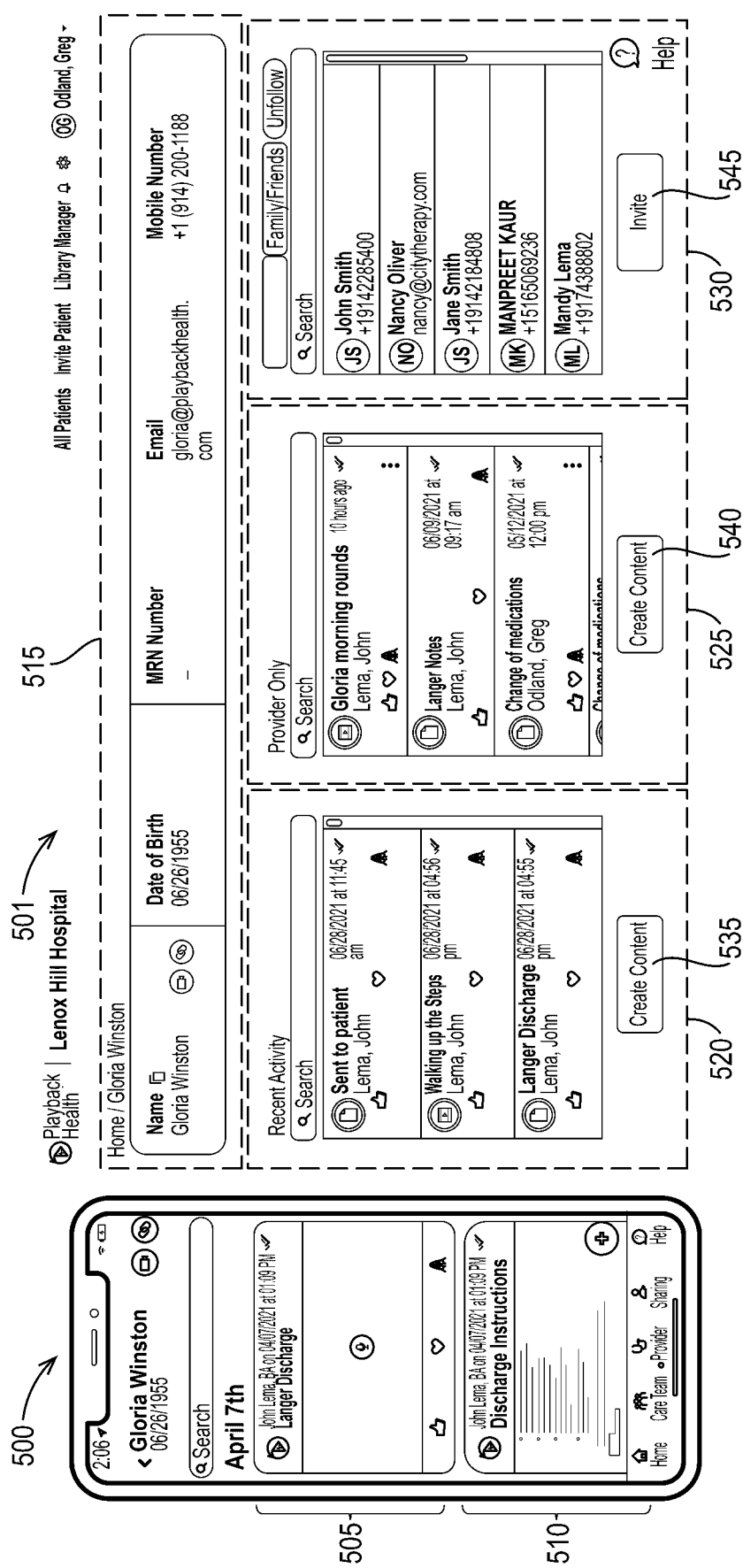
FIG. 5 depicts an exemplary mobile interface and an exemplary desktop interface for a clinician of the HCDP.

FIG. 5 depicts an exemplary mobile user interface (MUI) 500 and an exemplary desktop user interface (DUI) 501 of the HCDP 100. In this example, the MUI 500 and DUI 501 are generated based on a user role of a clinician. As shown, the MUI 500 is similar to the UI described with reference to FIG. 3. In this example, the MUI 500 is displaying a voice note (e.g., as indicated by a voice icon) 505 and a discharge instruction 510 for the patient "Gloria Winston."

The DUI 501 includes a patient information panel 515, a DHC list panel 520, a provider comment panel 525, and a contact list 530. The patient information panel 515 displays, in this example, a selected patient's name, date of birth, MRN number, email address, and phone number. The DHC list panel 520 displays a list of DHCs accessible by the user associated to the selected patient. In this example, the user may also select a create content button 535 to create new DHCs to associate with the selected patient.

In some implementations, based on the role of the user, the mobile application may provide different functions and/or authenticate different DHCs for access. As shown, the provider comment panel 525 may be displayed only when the user's role is a provider. In some examples, the CAS 105 may determine, based on a metadata of the comment DHCs, that the comments DHCs are only to be accessible to health provider. The provider comment panel 525 may, for example, include comments associated with the selected patient. As an illustrative example in FIG. 5, the provider comment panel 525 may include comments at observations made during a morning round. In some examples, the provider comment panel 525 may include a note regarding a change in medication for the selected patient. In this example, the user may also select a create content button 540 to create new comment to associate with the selected patient.

The contact list 530 displays a list of contacts associated with the selected patient. As shown, family and friends are displayed. The contact list 530 also includes another tab to display care team members of the selected patient. In this example, the user may select an invite button 545 to connect new member to associate with the selected patient.

Figure 6:
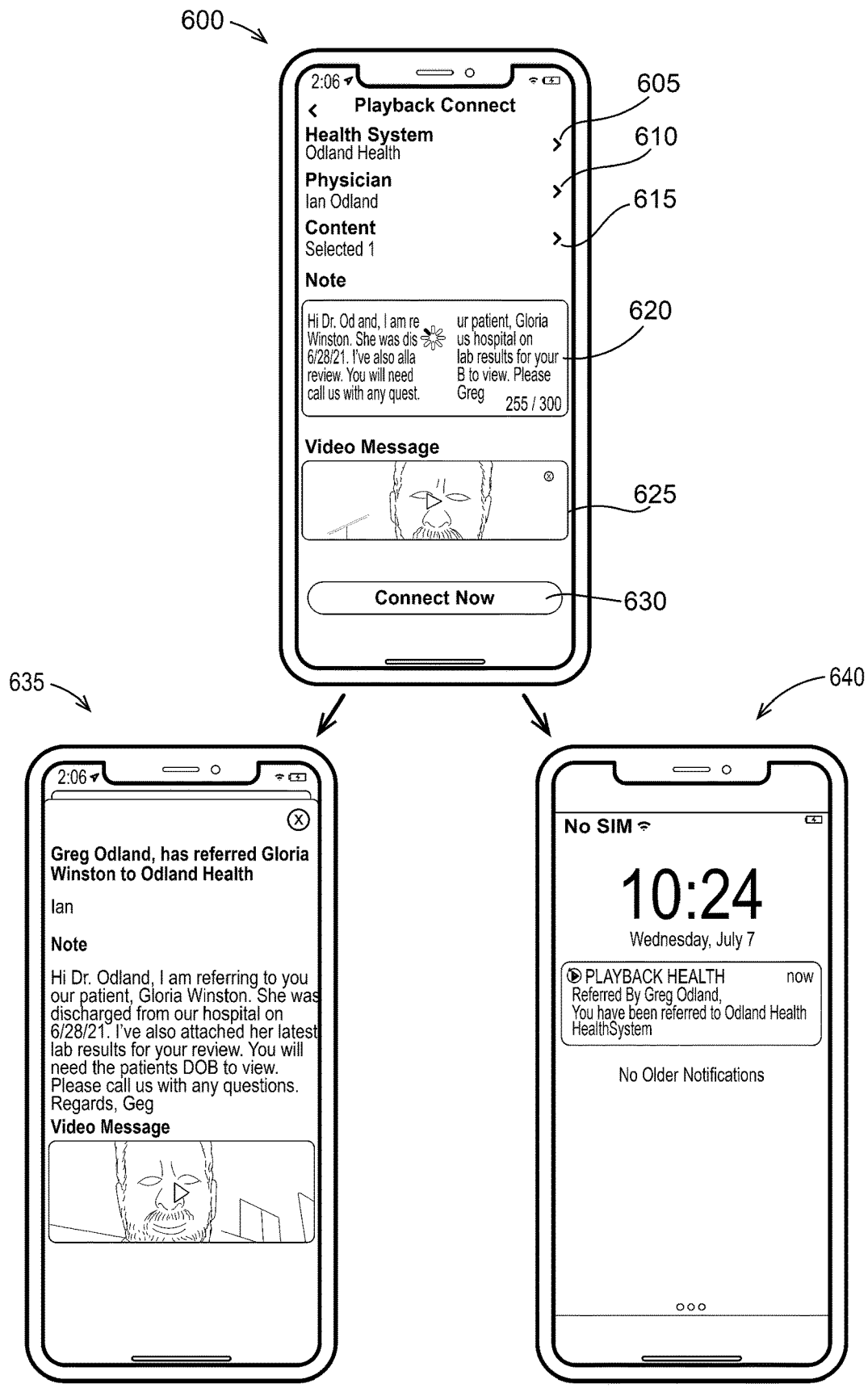
FIG. 6 depicts exemplary user interfaces of different stages in connecting a health provider to a patient.

FIG. 6 depicts exemplary user interfaces of different stages in connecting a health provider to a patient. For example, the different stages may be activated when a user select the connect button 315 to connect new member to the patient. In this example, a physician is referring a selected patient to an external physician to an external clinic.

As shown, upon a connect operation is initiated, the mobile application may display an invitation user interface 600. The invitation user interface 600 includes identification details of a person to be connected. In this example, the identification details include a health system 605 and a physician name 610. In some implementations, the health system 605 and the physician's name 610 may be selected from a predetermined list. For example, the predetermined list may be selected by an entity of the user.

The invitation user interface 600 also includes a DHC selection box 615. For example, the user may select one or more DHCs to be shared access with the connecting health provider. The invitation user interface 600 also includes notes 620 and a video message 625 to be sent together with an invitation message. After the invitation message is completed, the user may select a connect now button 630 to send the invitation message.

As shown, after the invitation message is received, a user interface 635 is displayed, in this example. In this example, when the user sends the invitation message, the patient receives a notification 640 that the patient is being referred. In some implementations, the referred physician may advantageously obtain full read and write access to the selected DHCs instantly.

In some implementations, a patient may also connect to other health providers in a similar process. For example, the patient may connect to another physician to grant access to DHCs associated with the patient.

Figure 7:
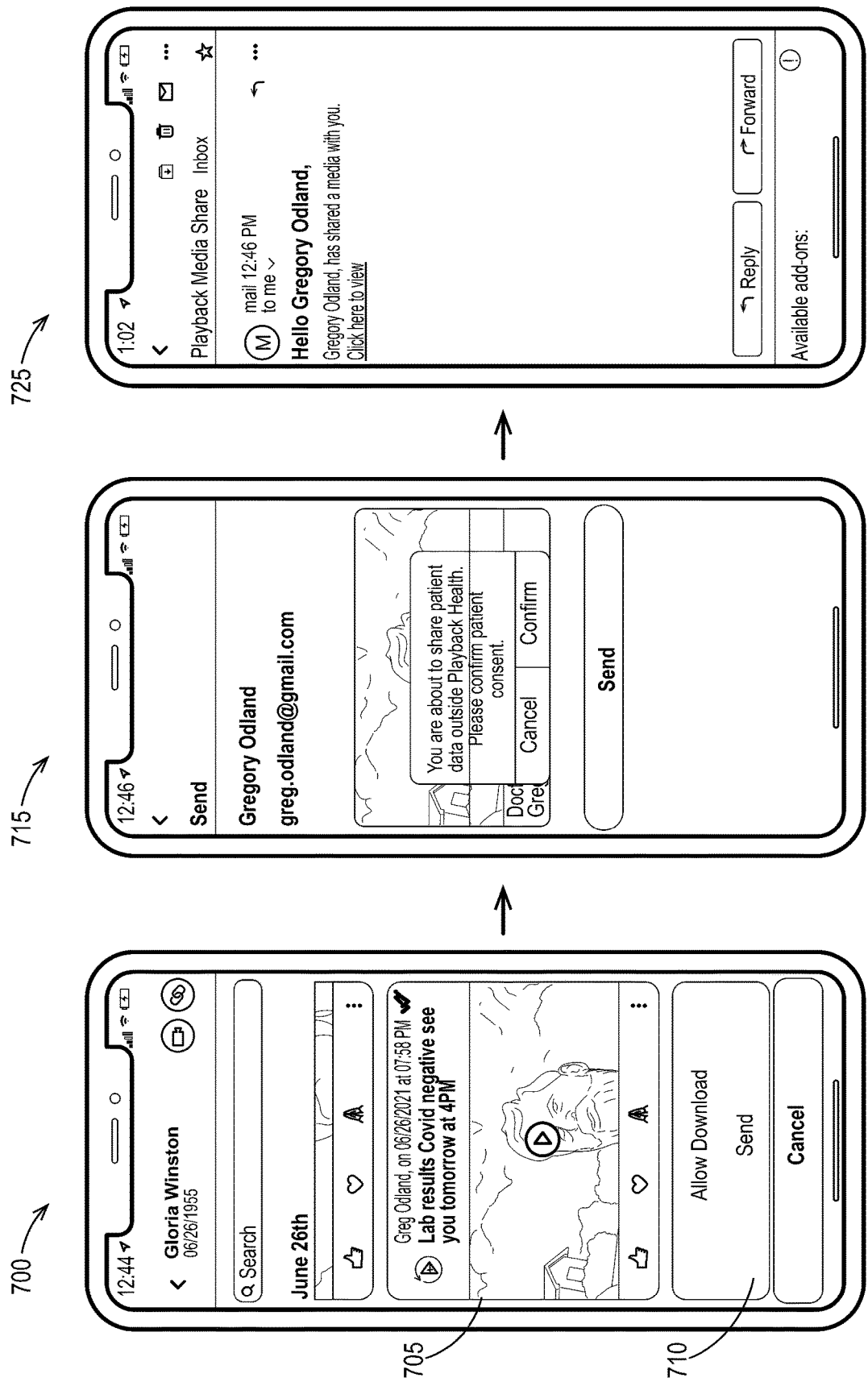
FIG. 7 exemplary mobile display of different stages in sharing a digital health content to other clinicians.

FIG. 7 exemplary mobile display of different stages in sharing a DHC to other clinicians. For example, the mobile display may be activated when the share button 335 (FIG. 3) is selected. In some implementations, the share button 335 may allow the user to transmit access right to a specific DHC via a text message link or email. For example, the user may share view access to one or more DHCs to individuals who are not users of the HCDP 100.

As shown in FIG. 7, a video DHC 705 is selected to be sent as shown in a display 700. Upon the user select a send button 710, a display 715 is shown, in this example. As shown, the display 715 includes a warning 720 that the user is sharing the video DHC 705 outside of the HCDP 100. After the video DHC is shared, in this example, a display 725 is shown at a receiver device. As shown, the display 725 includes a link 730 to the shared DHC. In some implementations, the link 730 may include a time-limited unique code. For example, the unique code may be valid for 24 hours. In some examples, upon selecting the link 730, the CAS 105 may validate the code and an expiration time of the code. In some implementations, the CAS 105 may also request the patient's date of birth as a second factor authorization check. In some implementations, if both the code and the second factor authorization are validated, the CAS 105 may transmit, to the receiver device, a link to view the shared DHC to be displayed in web browsers.

Figure 8:
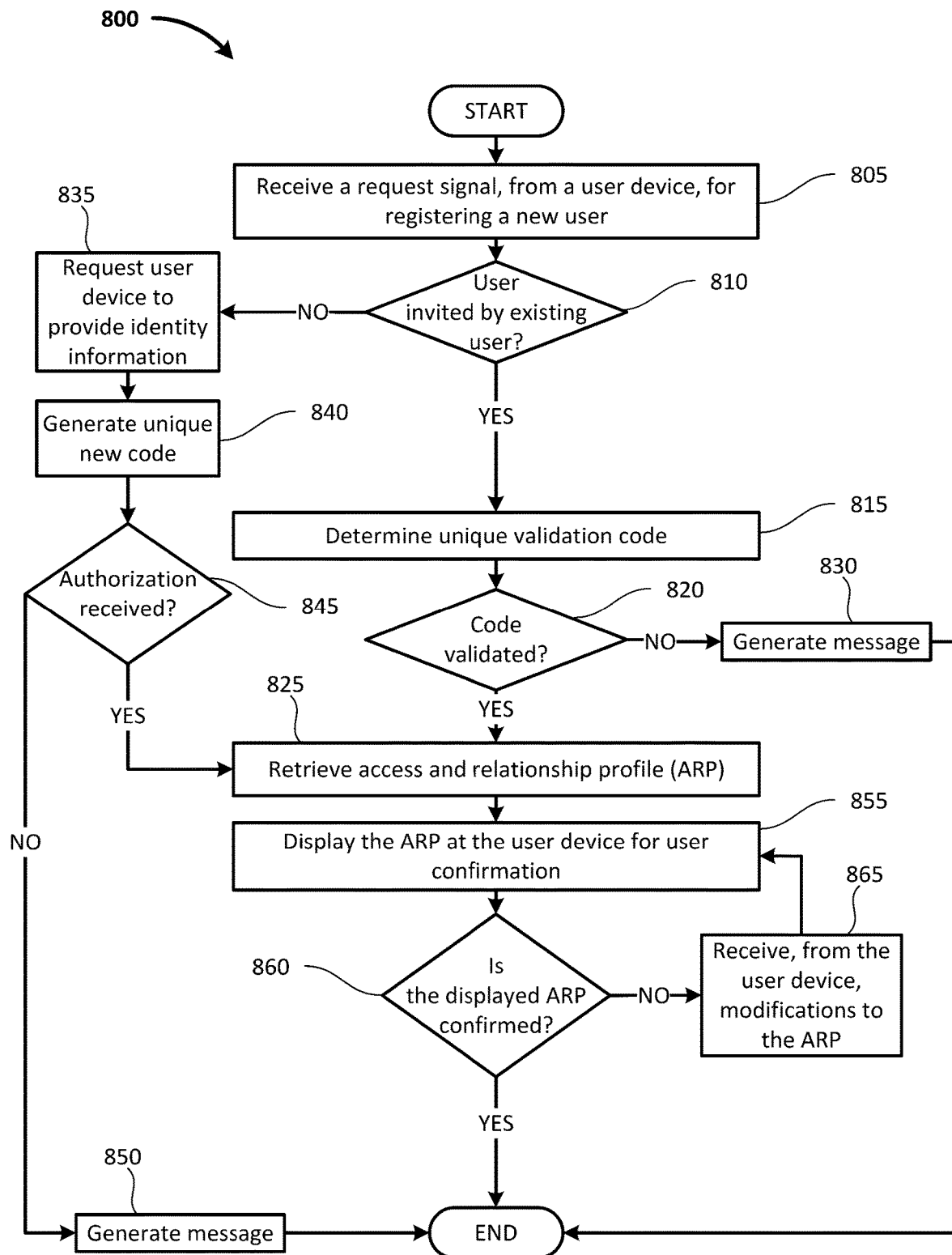
FIG. 8 is a flowchart illustrating an exemplary user registration method at the HCDP.

FIG. 8 is a flowchart illustrating an exemplary user registration method 800 at the HCDP 100. For example, the user registration method 800 may be performed by the AME 245.

The user registration method 800 starts when a request signal, from a user device, is received for registering a new patient in a step 805. For example, the user device may use a mobile application for accessing the HCDP 100 to register a new account. For example, the user may have downloaded a corresponding application to the user device (e.g., from an app store) and attempt to register an account. In some implementations, for example, the user may have responded to an invitation (e.g., a physical invitation from a provider using a QR code with a unique code, a digital invitation from a provider with a unique code, an electronic invitation message from a patient).

Upon receiving the request, it is determined, in a decision point 810, whether the user corresponding to the user device was invited by an existing user (e.g., the patient, a care provider). For example, a user identity may be determined from the request signal and used to search for a corresponding user record and/or user invitation. In some implementations, for example, the request signal may be evaluated for a code corresponding to an invitation identification (e.g., a unique invitation identifier having a predetermined association with a stored invitation from an existing user associated with an invited user).

If yes, then a unique validation code is determined in a step 815. For example, the unique validation code may have been transmitted by the user device in and/or with the request signal. In some implementations, a unique code may be generated (e.g., using an authentication system) and transmitted to the user to send to validate the registration request. For example, a provider may provide a patient with the unique code (e.g., through a QR code). In some implementations, the user may be prompted to enter the unique validation code. In a decision point 820, it is determined whether the (unique validation) code is validated. For example, the unique validation code may be compared against a predetermined validation criterion (e.g., code, algorithm, key) associated with the predetermined invitation. In some implementations, the code may, for example, be validated by confirmation from a user device associated with the entity generating the invitation.

If it is determined, in the decision point 820, that the code is validated, then an access and relationship profile (ARP) associated with the patient is retrieved in a step 825. In some implementations, the ARP may, for example, be generated (e.g., from a default ARP, if the ARP does not already exist).

For example, the ARP may be generated based on default data retrieved from external servers and/or predetermined rules of a healthcare enterprise associated with the patient. For example, the ARP may be populated based on rules set by a hospital that invites the patient to join the HCDP 100.

If the code is not validated in the decision point 820, then a message(s) is generated in a step 830. For example, the message may include an electronic message generated for display to the user requesting registration that registration was not successfully completed. In some implementations, for example, the message may include an (electronic) notification to an administrator (e.g., the inviting entity) that a failed attempt to register associated with the invitation has occurred and been associated with the invitation.

If, in the decision point 810, it is determined that the user was not invited (e.g., no predetermined invitation was found, the user device generated a signal corresponding to user input that the registration request is not associated with an invitation), then a signal is transmitted, in a step 835, to the user device to request the user to provide identity information. As an illustrative example, the user may be prompted for information such as, by way of example and not limitation, name, phone number, email address, location (e.g., address, city, state), date of birth, or some combination thereof. In some implementations, for example, the user may be requested to setup a unique username and password. For example, the user device may be requested to provide a mobile phone number for sending 2FA secure information. In some examples, the user device may be requested to pair an authentication application with the HCDP 100 to provide 2FA information.

In a step 840, a unique new code is generated (e.g., by the HCDP 100) in response to receiving the user identifying information. The unique code may, for example, be unique to the user, the user device, and/or a registration session. The unique code may, for example, be provided to a device of another user (e.g., a healthcare provider associated with the patient, a patient associated with a family member trying to register). If is then determined, in a decision point 845, whether authorization is received. For example, authorization may require a known (e.g., predetermined) existing user and/or user device associated with the patient providing the unique code. For example, a healthcare provider (e.g., hospital, enterprise) may be required to provide a validation code and/or signal authorizing registration of the patient (e.g., confirming an identity of the patient) within a (predetermined) time window (e.g., 1 hour, 30 minutes, 15 minutes, 5 minutes). In some examples, a patient may, for example, be required to provide a validation code and/or signal authorizing registration and/or association of a new healthcare provider and/or friend/family member with the patient's records (e.g., confirming identify of the requesting user).

If it is determined that authorization is received, in the decision point 845, then the user registration method 800 proceeds to the step 825. If is determined, in the decision point 845, that authorization is not received, then the user registration method 800 generates a message in a step 850. For example, the message may include a notification to the requesting user device that registration was unsuccessful (e.g., including indications of potential next steps). In some implementations, the message may include a notification to predetermined user(s) and/or device(s) of a failed attempt (e.g., associated with a predetermined patient record but not validated).

After the ARP is retrieved at the step 825, then the ARP is displayed at the user device for user confirmation in a step 855. For example, the ARP may display patient information. In some implementations, the ARP may, for example, correspond to 'care team' information (e.g., associated care providers, associated family, associated friends). After the ARP is displayed, it is determined whether the displayed ARP is confirmed in a decision point 860. For example, the displayed ARP may include a confirmation button for the patient to confirm. If the displayed ARP is not confirmed, then modifications to the ARP are received from the user device in a step 865 and the method returns to the step 855. If the displayed ARP is confirmed, then the user registration method 800 ends.

Figure 9:
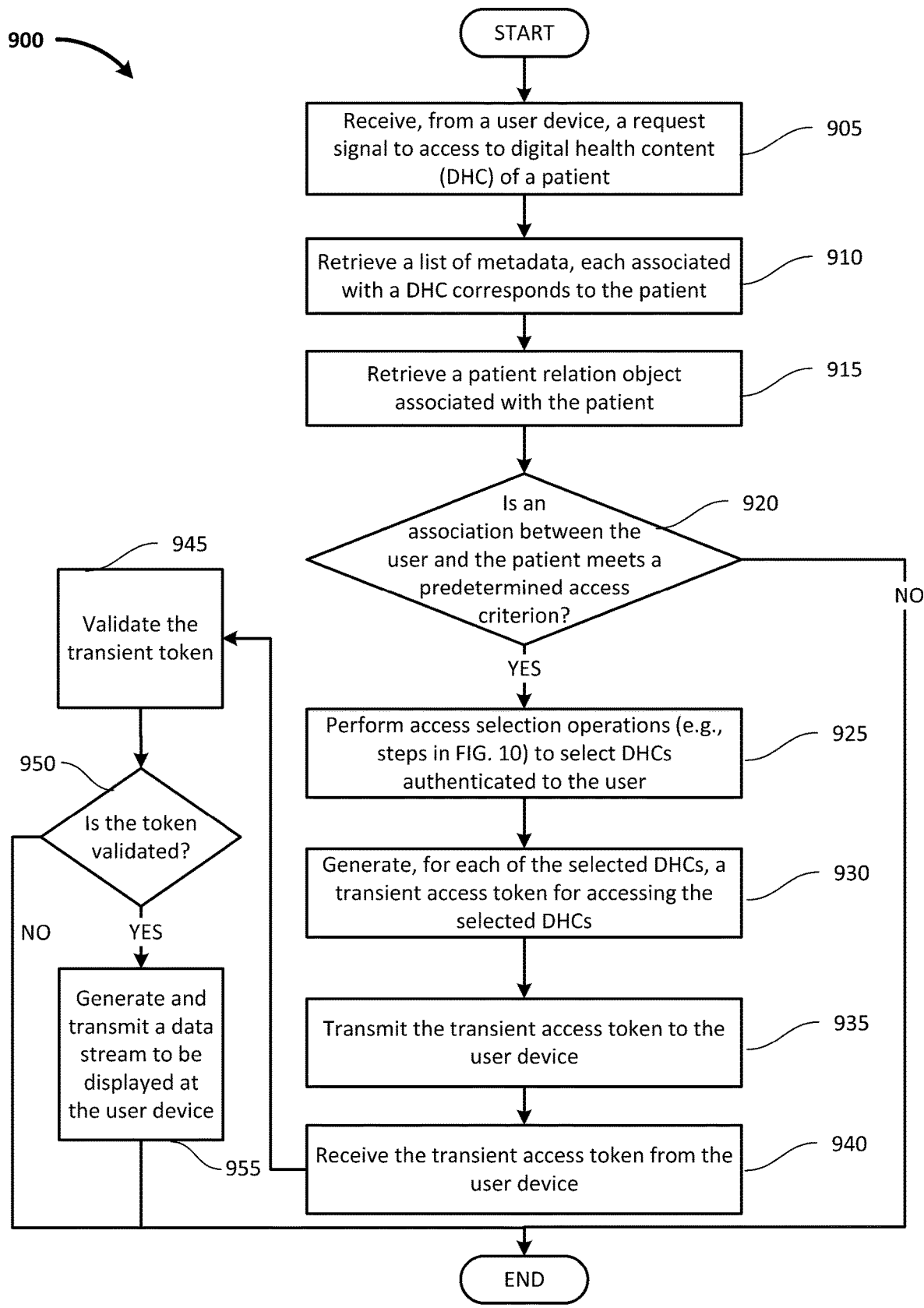
FIG. 9 is a flowchart illustrating an exemplary method for processing a request for temporal access to a patient's digital health content.

FIG. 9 is a flowchart illustrating an exemplary method 900 for processing a request for temporal access to a patient's digital health content. For example, the AAE 240 may process the request for accessing a patient's DHCs. The method 900 starts when, from a user, a request is received to access to digital health content (DHC) of a patient in a step 905. Next, a list of metadata, each associated with a DHC corresponds to the patient are retrieved in a step 910. For example, the list of DHCs associated with the patient may be stored in the DHC metadata database 270.

A patient relation object associated with the patient is retrieved in a step 915. For example, the patient relation object may be retrieved from the authentication object database 275. In some implementations, the patient relation object may include a topology object of computer readable instructions for determining access rights of each DHCs corresponding to a user. Next, it is determined whether an association between the user and the patient meets a predetermined access criterion in a decision point 920. For example, the AAE 240 may compare the patient relation object and the user identity. For example, the predetermined access criterion may include that the user is associated with the patient with a predetermined relationship to the patient as a member of a care team and/or a (predetermined) "family and friend" of the patient.

If it is determined that the association between the user and the patient does not meet a predetermined access criterion, then the method 900 ends.

If it is determined that an association between the user and the patient meets a predetermined access criterion, then access selection operations are performed to select DHCs authenticated to the user in a step 925. Some exemplary access selection operations are described with reference to FIG. 10. After the access selection operations are performed to select authenticated DHCs, for each of the selected DHCs, a transient access token for accessing the selected DHCs is generated in a step 930. Upon the transient access token being generated, the transient access token is transmitted to the user device in a step 935. In some implementations, by way of example and not limitation, multiple tokens may be generated and transmitted together (e.g., in a single message) to the user device.

Next, the transient access token is received from the user device in a step 940. For example, the user of the user device may select a link containing the transient token to display the associated DHC. Upon receiving the transient token, the transient token is validated in a step 945. For example, the TAE 255 may perform validate operations to validate the transient token. If the transient token is not validated in decision point 950, the method ends. If the transient token is validated in the decision point 950, then a data stream is generated (e.g., by the display engine 258) and transmitted to be displayed at the user device in a step 955 and the method 900 ends.

Figure 10:
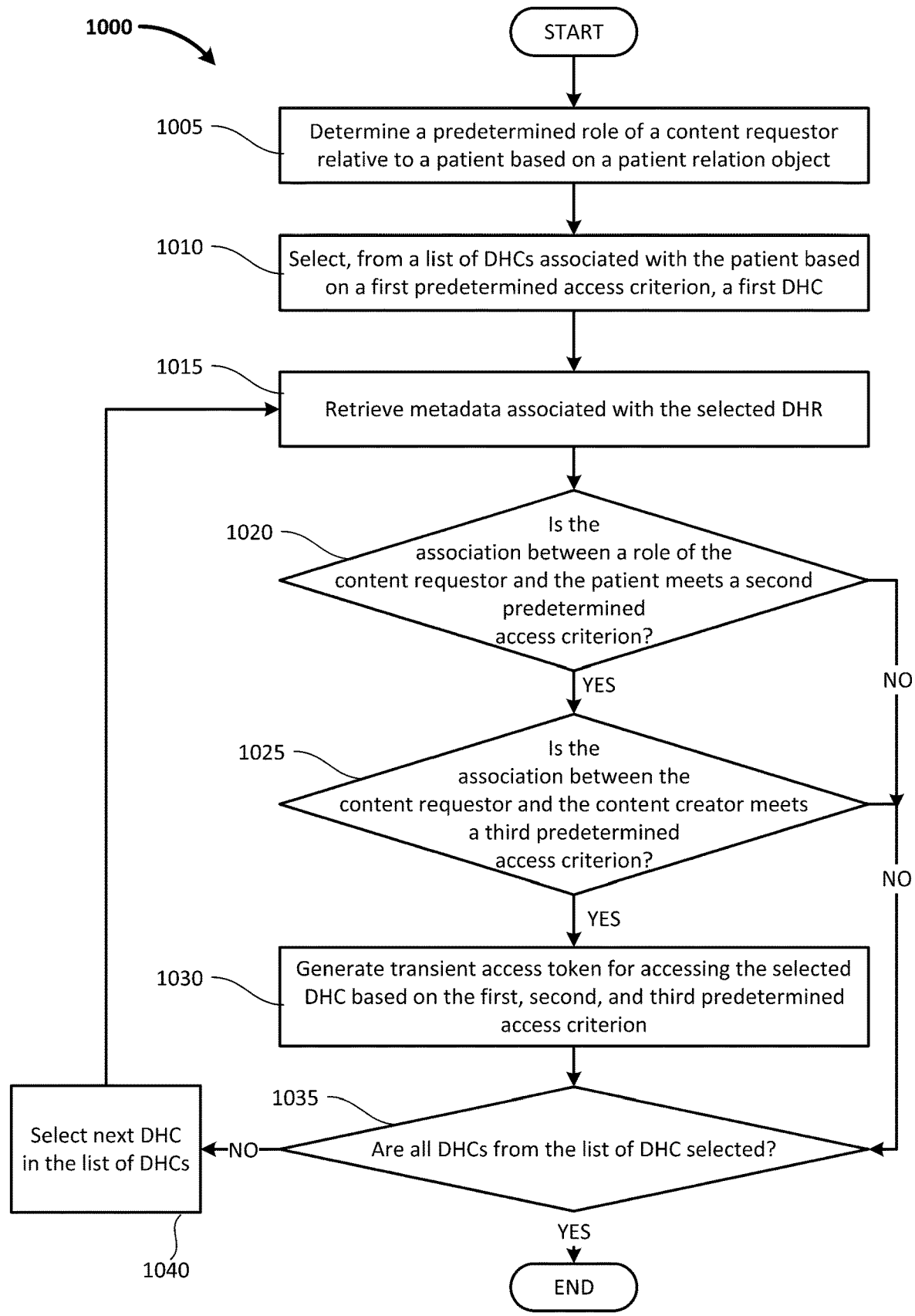
FIG. 10 is a flowchart illustrating an exemplary method for authenticating access health content of a patient from a requestor.

FIG. 10 is a flowchart illustrating an exemplary method 1000 for authenticating access health content of a patient from a requestor. For example, the method 1000 may be executed when access selection operations are be performed to select, from a list of DHCs, one or more authenticated DHCs to the requestor. The method 1000 starts when a predetermined role of a content requestor relative to a patient based on a patient relation object is determined in a step 1005. Next, from a list of DHCs associated with the patient based on a first predetermined access criterion, a first DHC is selected in a step 1010. For example, the list of the DHCs may be selected based on a result of the decision point 920 as described in FIG. 9. Then, metadata associated with the selected DHR is retrieved in a step 1015. For example, the metadata is retrieved from the DHC metadata database 270.

After the metadata is retrieved, it is determined whether an association between a role of the content requestor and the patient meets a second predetermined access criterion in a decision point 1020. For example, the second predetermined access criterion of the selected DHC may be defined in the retrieved metadata. For example, the retrieved metadata may indicate that the selected DHC may be accessed by medical doctors but not by nurses. If it is determined that the association between the role of the content requestor and the patient meets the second predetermined access criterion, then it is determined whether an association between the content requestor and the content creator meets a third predetermined access criterion in a decision point 1025. For example, the third predetermined access criterion may allow the content requestor in the same enterprise of the content creator to be granted access to the selected DHC.

If it is determined that the association between the content requestor and the content creator meets a third predetermined access criterion, then a transient access token is generated for accessing the selected DHC based on the first, second, and third predetermined access criterion in a step 1030. After the transient token is generated, it is determined whether all DHCs from the list of DHC are selected in a decision point 1035. If all DHCs from the list of DHC are selected, then the method 1000 ends. If not all DHCs from the list of DHC are selected, then next DHC in the list of DHCs are selected in a step 1040 and the method 1000 returns to the step 1015.

If, at the decision point 1020, it is determined that the relation between the role of the content requestor and the patient does not meet the second predetermined access criterion, the method 1000 proceeds to the decision point 1035. If at the decision point 1025, it is determined that the relation between the content requestor and the content creator does not meet a third predetermined access criterion, the method 1000 proceeds to the decision point 1035.

Figure 11:
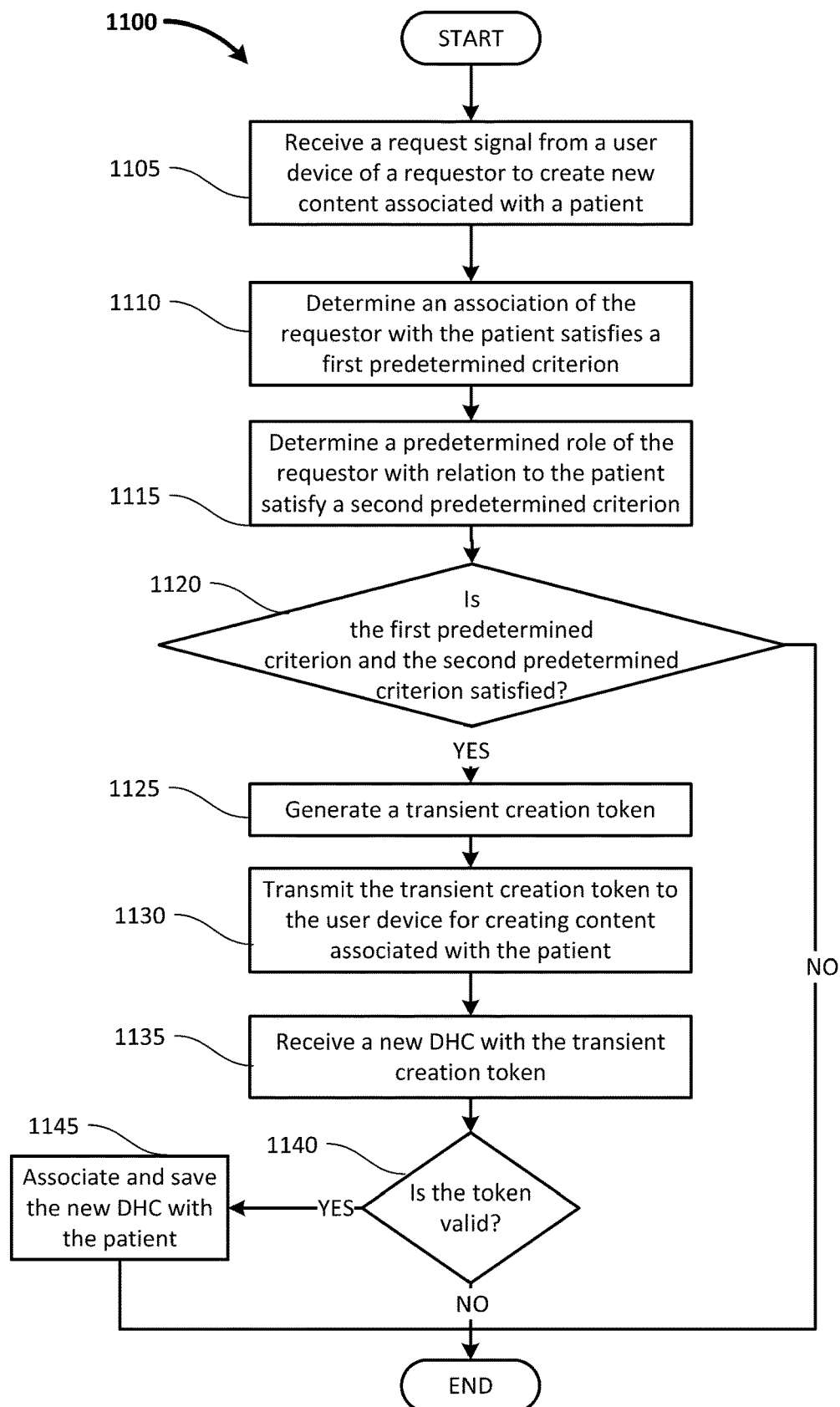
FIG. 11 is a flowchart illustrating an exemplary health content creation method at the HCDP.

FIG. 11 is a flowchart illustrating an exemplary health content creation method 1100 at the HCDP 100. For example, the method 1100 may be activated when a user selects the create button 325 of the UI 300. In this example, the method 1100 starts when a request signal is received from a user device of a requestor to create new content associated with a patient in a step 1105. Next, an association of the requestor with the patient satisfies a first predetermined criterion is determined in a decision point 1110. For example, the first predetermined criterion may require that the requestor and the patient have a common organization. For example, the requestor may be working at a clinic visited by the patient.

Next, a predetermined role of the requestor with relation to the patient satisfy a second predetermined criterion is determined in a step 1115. For example, the second predetermined criterion may require that the role of the requestor may be a nurse or a physician with relation to the patient. In some implementations, the patient may, for example, only be able to view content created by the enterprise that the physician is associated with (e.g., the physician's hospital). The enterprise associated with creating the content may, for example, define access rights, roles, and/or privileges.

Next, it is determined whether the first predetermined criterion and the second predetermined criterion satisfied in a decision point 1120. If it is determined that the first predetermined criterion and the second predetermined criterion are not satisfied, the method 1100 ends. If, at the decision point 1120, it is determined that the first predetermined criterion and the second predetermined criterion are satisfied, then a transient creation token is generated in a step 1125. For example, the transient creation token may be a time-sensitive token allowing the user device of the requestor to associate a DHC with the patient within a predetermined time (e.g., 30 minutes). After the transient creation token is generated, the transient creation token is transmitted to the user device of the requestor for creating content associated with the patient in a step 1130.

After the transient creation token is transmitted, a new DHC with the transient creation token is received in a step 1135. For example, the requestor may create a video using the UI 400 as described with reference to FIG. 4 to create a new DHC associate with the patient. For example, then the new DHC is sent, the user device of the requestor may send the transient creation token with the DHC. Next, it is determined whether the transient creation token is valid at a decision point 1140. For example, the TAE 255 may verify the validity of the received transient creation token. If it is determined that the transient creation token is not valid, the method 1100 ends. If it is determined that the transient creation token is valid, then the new DHC is saved and associated with the patient in a step 1145 and the method 1100 ends. For example, the CAS 105 may save the new DHC to the SCS 110 and create metadata to associate the new DHC with the patient.

Figure 12:
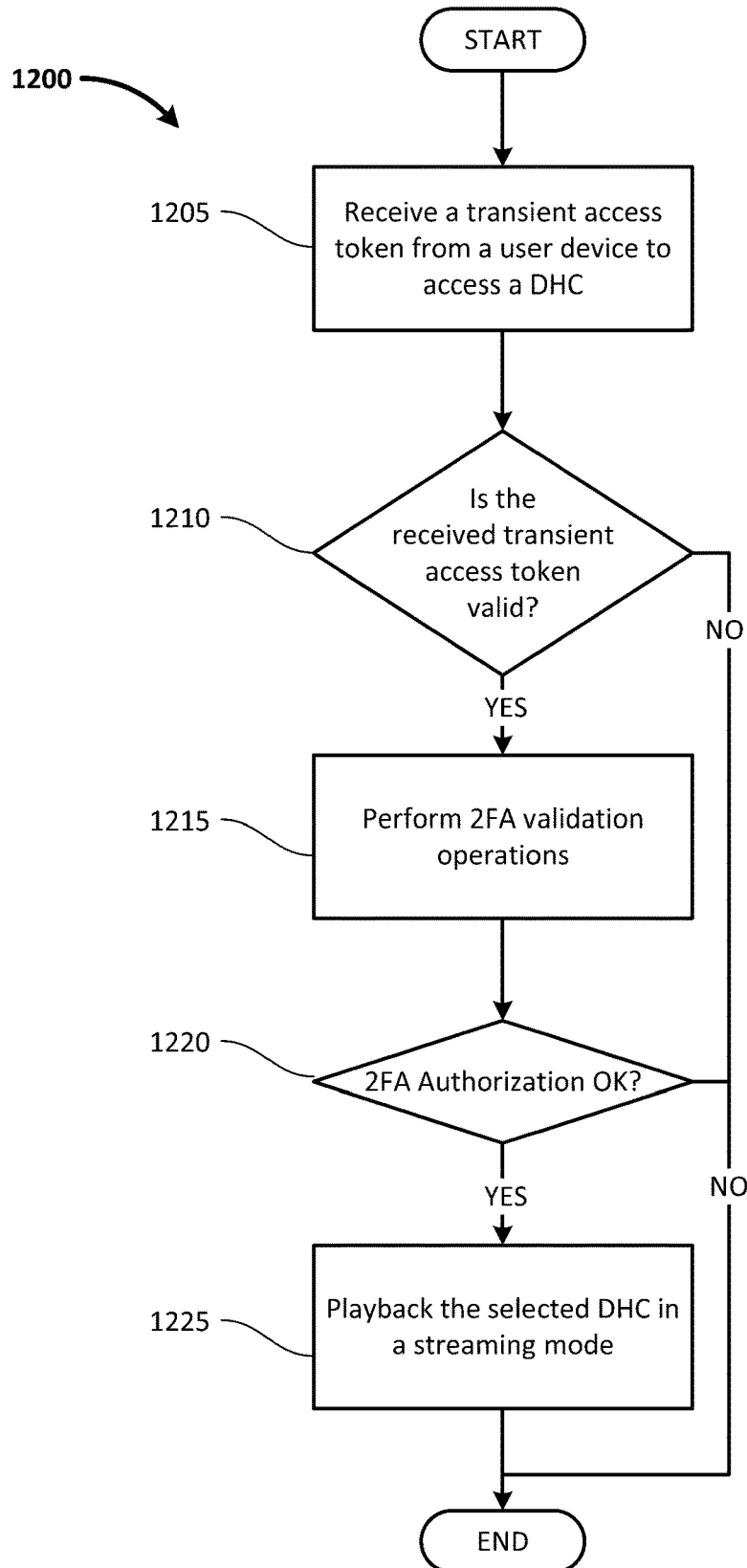
FIG. 12 is a flowchart illustrating an exemplary secure content playback method at the HCDP.

FIG. 12 is a flowchart illustrating an exemplary secure content playback method 1200 at the HCDP 100. For example, the secure content playback method 1200 may be activated when a user selects one of the DHCs 305a, 305b described with reference to FIG. 3. In this example, the secure content playback method 1200 starts when a transient access token from a user device to access a DHC is received in a step 1205. Next, it is determined whether the received transient access token is valid in a decision point 1210. For example, the TAE 255 may validate the received transient access token.

If it is determined that the received transient access token is valid, then a 2FA validation operations is performed in a step 1215. For example, the CAS 105 may use the 2FA server 220 to verify an identity of the user. Then, it is determined whether the 2FA Authorization is successful in a decision point 1220. If it is determined that the 2FA authorization is successful, then the selected DHC is played back in a streaming mode in a step 1225 and the method 1200 ends.

If it is determined that the received transient access token is not valid in the decision point 1210, then the method 1200 ends. If, in the decision point 1220, it is determined that the 2FA authorization is not successful, then the method 1200 ends.

Figure 13:
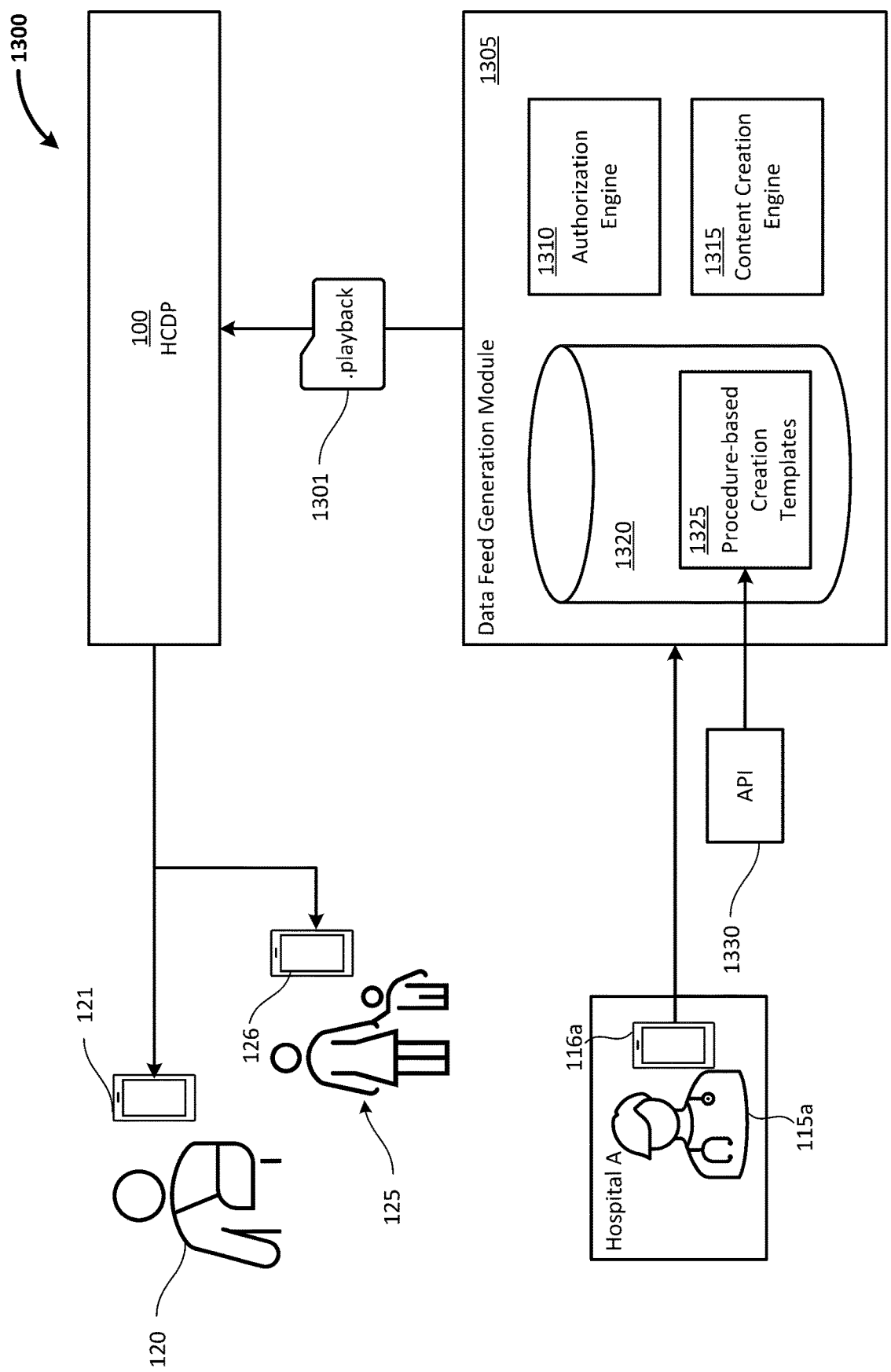
FIG. 13 is a block diagram depicting an exemplary Procedural Data Feed System (PDFS).

FIG. 13 is a block diagram depicting an exemplary Procedural Data Feed System (PDFS 1300). For example, a physician (e.g., the physician 115a described in FIG. 1) may use the PDFS 1300 to create a media annotated medical content 1301 (e.g., a media guided discharge instruction) for a patient. In this example, the PDFS 1300 includes the HCDP 100 and a Data Feed Generation Module (DFGM 1305). For example, the patient 120 or the family members 125 may access, using the devices 121 or 126 and the time-limited tokens, the media annotated medical content 1301 created by the physician 115a via the HCDP 100.

The DFGM 1305 includes an authorization engine 1310, a content creation engine 1315, and a data storage 1320. In some implementations, the authorization engine 1310 may authenticate the physician 115a for creating content for the patient 120. For example, the authorization engine 1310 may be configured to communicate, via an API, with the AAE 240 to authenticate the physician 115a. In some implementations, the authorization engine 1310 may request and store a time-limited creation token corresponding to the device 116a for generating the media annotated medical content 1301. The data storage 1320 includes Procedure-based Creation Templates (PBCT 1325). In some implementations, the PBCT 1325 may include a collection of sections of instructions for a medical procedure. In some examples, the collection of sections may be time-sensitive. For example, some sections may require a patient to complete before a predetermined time. In some implementations, the PBCT 1325 may correspond to at least some portion(s) (e.g., predetermined data types) from an Admission Discharge Transfer Feed (ADTF). The ADTF may include, for example, discharge instructions for a patient from a pre-selected hospital (e.g., the hospital A of the physician 115a). In some examples, the ADTF may include follow-up appointments, medication instructions, and/or other care instructions. In various implementations, the ADTF may include data templates of predetermined discharge instructions to be presented digitally on a mobile device of a discharged patient.

In some implementations, the data storage 1320 may be connected to an external API 1330. For example, the DFGM 1305 may retrieve, using the external API 1330, predetermined medical data including, by way of example without limitation, discharge medications, pre-written doctor notes, and/or diet recommendations. For example, the hospital A may include, for a patient discharged from a broken arm, a set of predetermined notes for the patient that is accessible via the external API 1330. In some implementations, the DFGM 1305 may be configured retrieve the predetermined notes to generate the PBCT 1325 for the patient.

Using the PBCT 1325, in some implementations, the content creation engine 1315 may include procedures to present and guide the physician 115a to generate a guided medical content. For example, the content creation engine 1315 may, for each section, generate a digital display to the device 116a and allow the physician 115a to add audio or video rendering to the section. In various implementations, the physician 115a may use the DFGM 1305 to advantageously generate a contextually based representation of instructions (e.g., with audio or video rendering). In the depicted example, the instructions are discharge instructions.

In some implementations, by way of example and not limitation, the content creation engine 1315 and/or the DFGM 1305 may provide annotation as disclosed at least with reference to FIGS. 1-31 of U.S. application Ser. No. 16/876,083 and FIGS. 1-31 of PCT Application Serial No. PCT/US2020/033328, the entire contents of which are incorporated herein by reference.

In this example, the content creation engine 1315 generates, based on the media received from the device 116a and the PBCT 1325, the media annotated medical content 1301. For example, the content creation engine 1315 may generate using the PBCT 1325 and the received media content from the physician 115a to generate a ".playback" file. The file may include a data structure (e.g., in a JavaScript Object Notation (JSON) or in an Extensible Markup Language format, or other public or proprietary data formats) of reference pointers to locate (relative) memory address of each medica content corresponds to each section in the PBCT 1325.

As shown, users (e.g., the patient 120 or the family members 125) may access the annotated medical content 1301 via the HCDP 100. For example, the patient 12 may access the media annotated medical content 1301 using a mobile application installed in the device 121 (e.g., by executing the method 900 and the method 1200).

Various embodiments may, for example, advantageously provide a technical solution to the problem of generating a targeted media guided and specifically annotated EMR for patients. In some examples, when a patient is discharged from a hospital, without a procedure related information presentation system, a clinician may be required to access a EMR content server, retrieve a specific EMR Discharge Instructions for the patient, print out the specific EMR Discharge Instructions, and physically hands off to patient as physical document. In some examples, the documents may include more than twenty pages. To explain the lengthy document, for example, a clinician (e.g., a nurse) may need to go over the document page by page with the patient in person.

Using the PDFS 1300, for example, the EMR Discharge Instructions may be incorporated within the media annotated medical content 1301 advantageously retrievable on demand from user devices. In some implementations, the user may also "playback" targeted media guidance recorded by health professional explaining the details of the discharge instructions.

Figure 14:
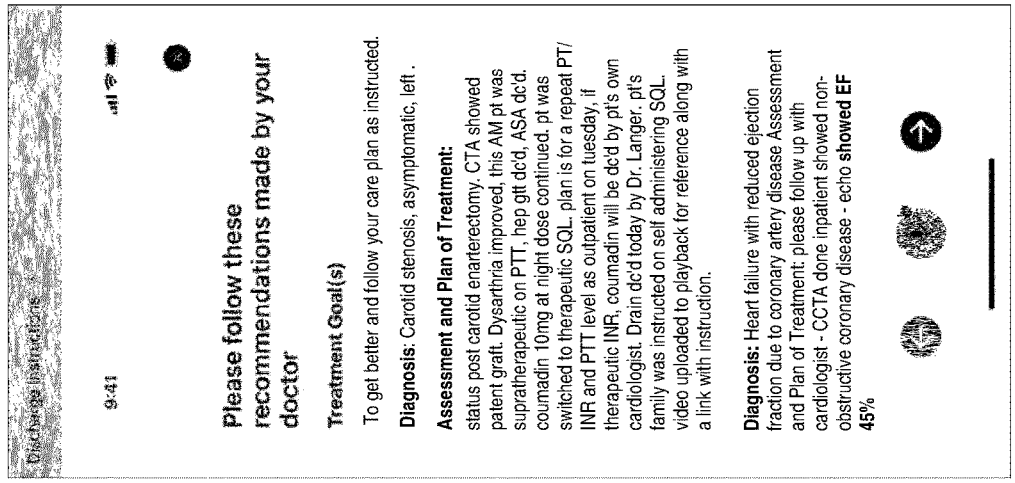
FIG. 14, FIG. 15, FIG. 16, and FIG. 17 are schematic diagram showing exemplary user interface for creating a media annotated media content
Figure 14:

FIG. 14, FIG. 15, FIG. 16, and FIG. 17 are schematic diagram showing exemplary user interface for creating a media annotated media content. As shown in FIG. 14, a UI 1400 is displayed for creating a discharge instruction. For example, the device 116a of the physician 115a may display the UI 1400 when the physician 115a is creating discharge instructions for the patient 120. In this example, the UI 1400 is displaying a section of the discharge instructions relating to follow up appointments. A clinician may use a record button 1405 to record media (e.g., voice) guidance related to this section. For example, the clinician may include important observations to be reported to each of the appointments. In some examples, the clinician may include reminders for appointment schedule such as "It's really important you see Dr Salman in 24 hours, and follow up with Dr. Brown in the next couple weeks." When the clinician is finished annotating this section, the clinician may select a next button 1410 to a next screen.

Figure 15:
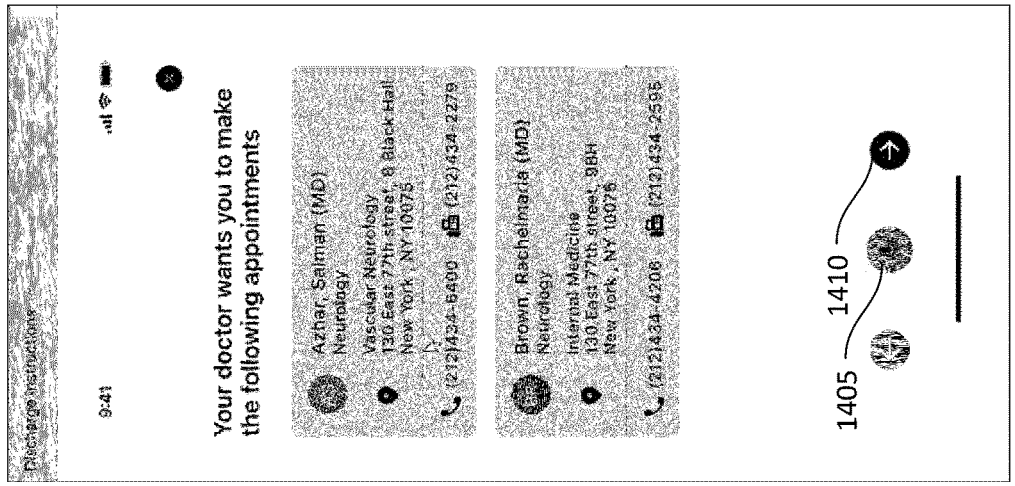
Figure 15:
Figures 16, 17:
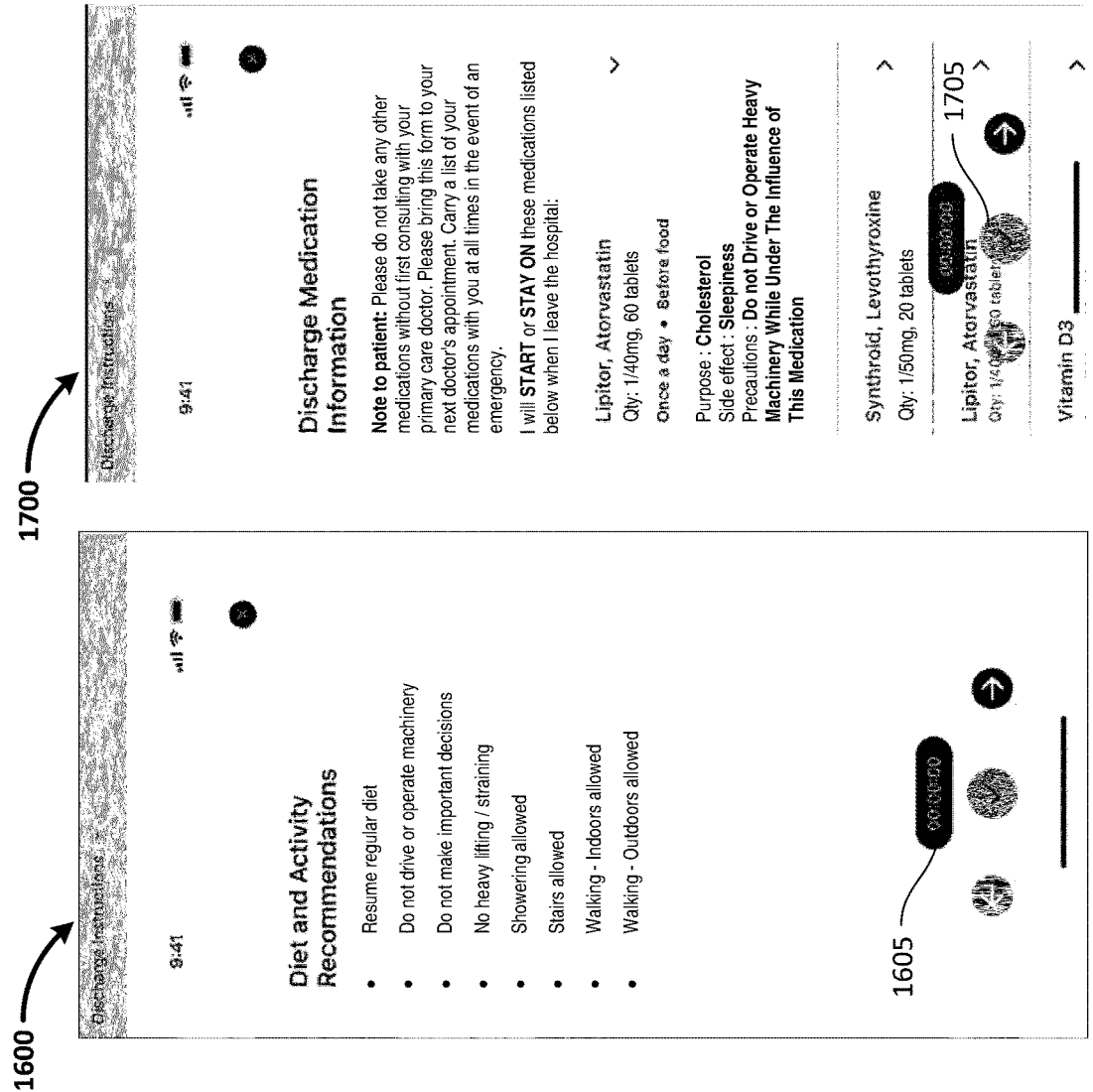

As shown in FIG. 15, the UI 1500 includes some additional insight/reminders about diagnosis, therapy, and other important information for a patient. As shown in FIG. 16, doctor's recommendations are displayed. In this example, a clinician is recording an audio using the UI 1600 (display as a time indicator 1605). As shown in FIG. 17, detailed information various medication is shown in a UI 1700. For example, additional explanations are depicted as being recorded. Once the clinician is complete, the clinician may, in the depicted example, use a complete recording button 1705 to end the recording. A media file may, for example, be created and/or updated (e.g., finalized, appended).

Figure 18:
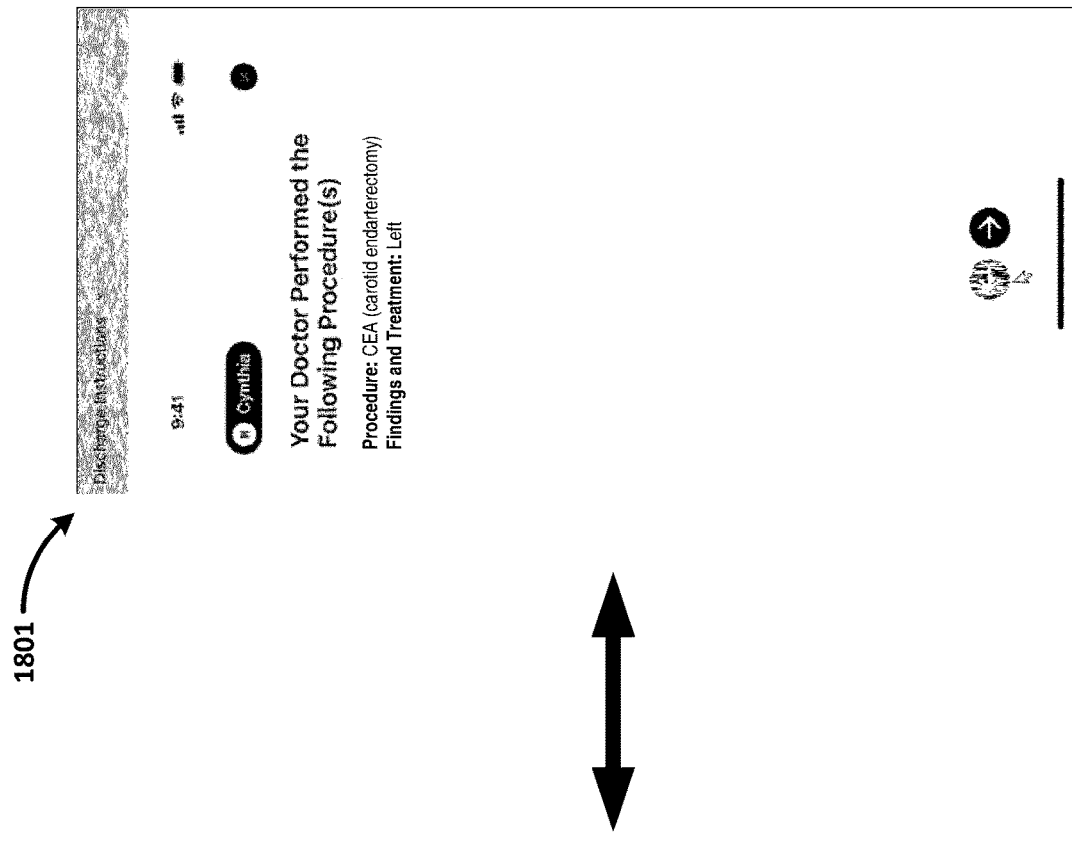
FIG. 18 depicts schematic diagrams of exemplary display for playing back a media annotated media content.

FIG. 18 depicts schematic diagrams of exemplary display 1800 for playing back a media annotated media content. As shown in this example, the display 1800 includes a playback button 1805. For example, a user may "playback" media content associated with the section currently in display by selecting the playback button 1805. The display 1800 also includes a backward button 1810 and a forward button 1815 for the user to browser through displayed content (e.g., from the display 1800 to a display 1801). For example, the display 1800 and the display 1801 may be screens, as depicted, in a discharge instructions (e.g., sequential screens). The user may, for example, be guided through the discharge instructions to be presented with corresponding visual display(s) and pre-associated media content.

Figure 19:
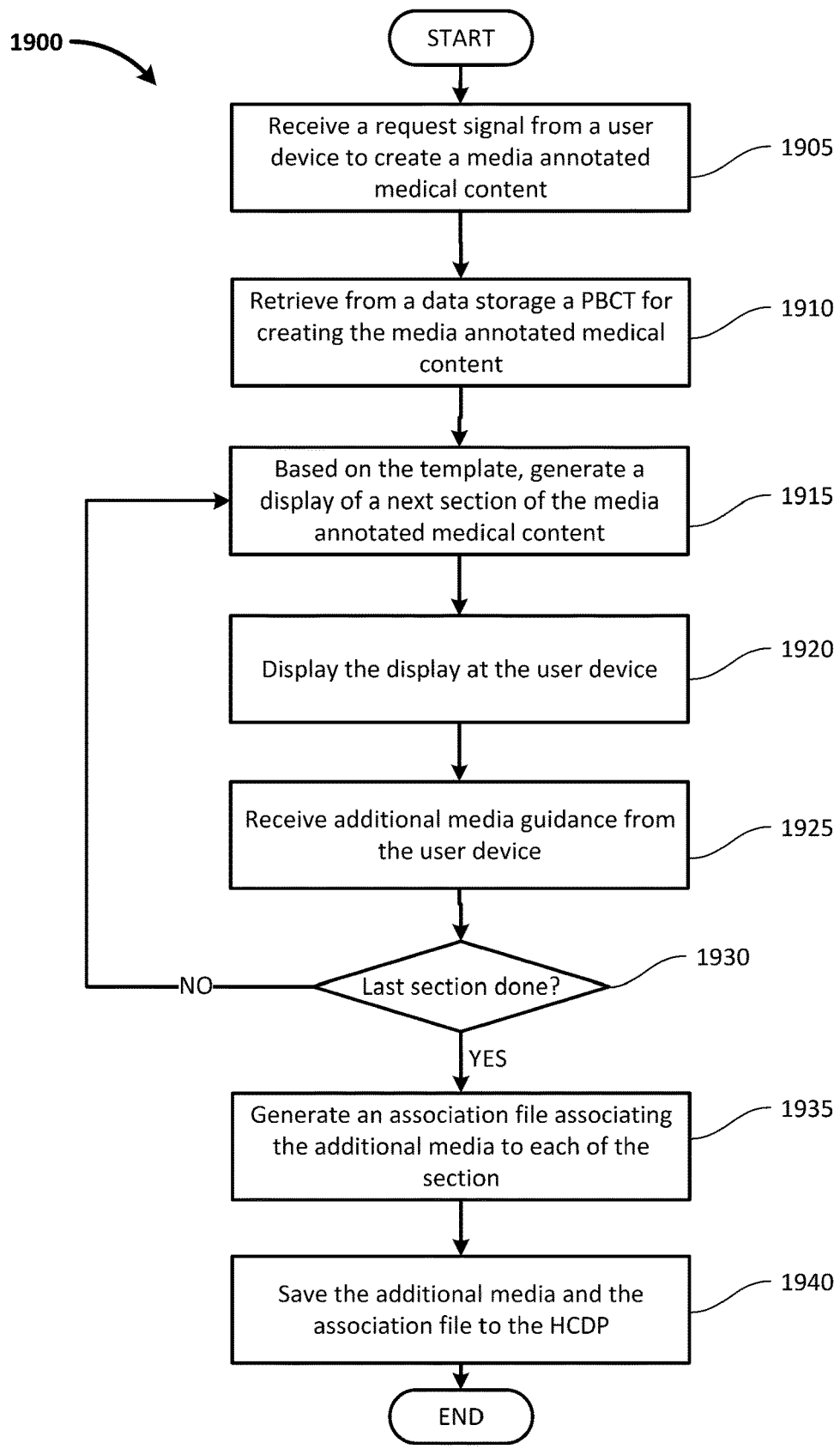
FIG. 19 is a flowchart illustrating an exemplary media annotated media content creation method.

FIG. 19 is a flowchart illustrating an exemplary media annotated media content creation method 1900. For example, the content creation engine 1315 may perform the method 1900 to generate the annotated medical content 1301 to be stored in the HCDP 100. The method 1900 begins when a request signal is received from a user device to create a media annotated medical content in step 1905. For example, the device 116a may be operated to generate discharge instructions for a patient. Next, in step 1910, a PBCT for creating the media annotated medical content is retrieved from a data storage. Based on the template, in step 1915, a display of a next section of the media annotated medical content is generated. In step 1920, the display is displayed at the user device. For example, the content creation engine 1315 may generate a display (e.g., the UIs 1400, 1500, 1600, 1700) using the PBCT to be displayed at the device 116a. Using the display, for example, a clinician may record media to annotate the displayed content.

In step 1925, additional media guidance from the user device is received. Next, it is determined whether the last section of the PBCT is done in a decision point 1930. If the last section of the PBCT is not done, the step 1915 is repeated. If the last section of the PBCT is done, an association file associating the additional media to each of the section is generated in step 1935. For example, a new filetype (e.g., ".playback", ".med", ".myhealthrecords," ".discharge") may be generated (e.g., as disclosed at least with reference to media annotated medical content 1301 shown in FIG. 13) to associate the additional media to each of the section in the PBCT.

After the file is generated, the additional media and the association file to the HCDP 100 is saved in step 1940, and the method 1900 ends. In some implementations, the content creation engine 1315 may use a time-limited creation token stored by the authorization engine 1310 to save the media annotated media content to the HCDP 100. For example, the patient 120 may use the device 121 to access the generated media annotated medical content and playback the media guidance device 121 using the HCDP 100.

Figure 20:
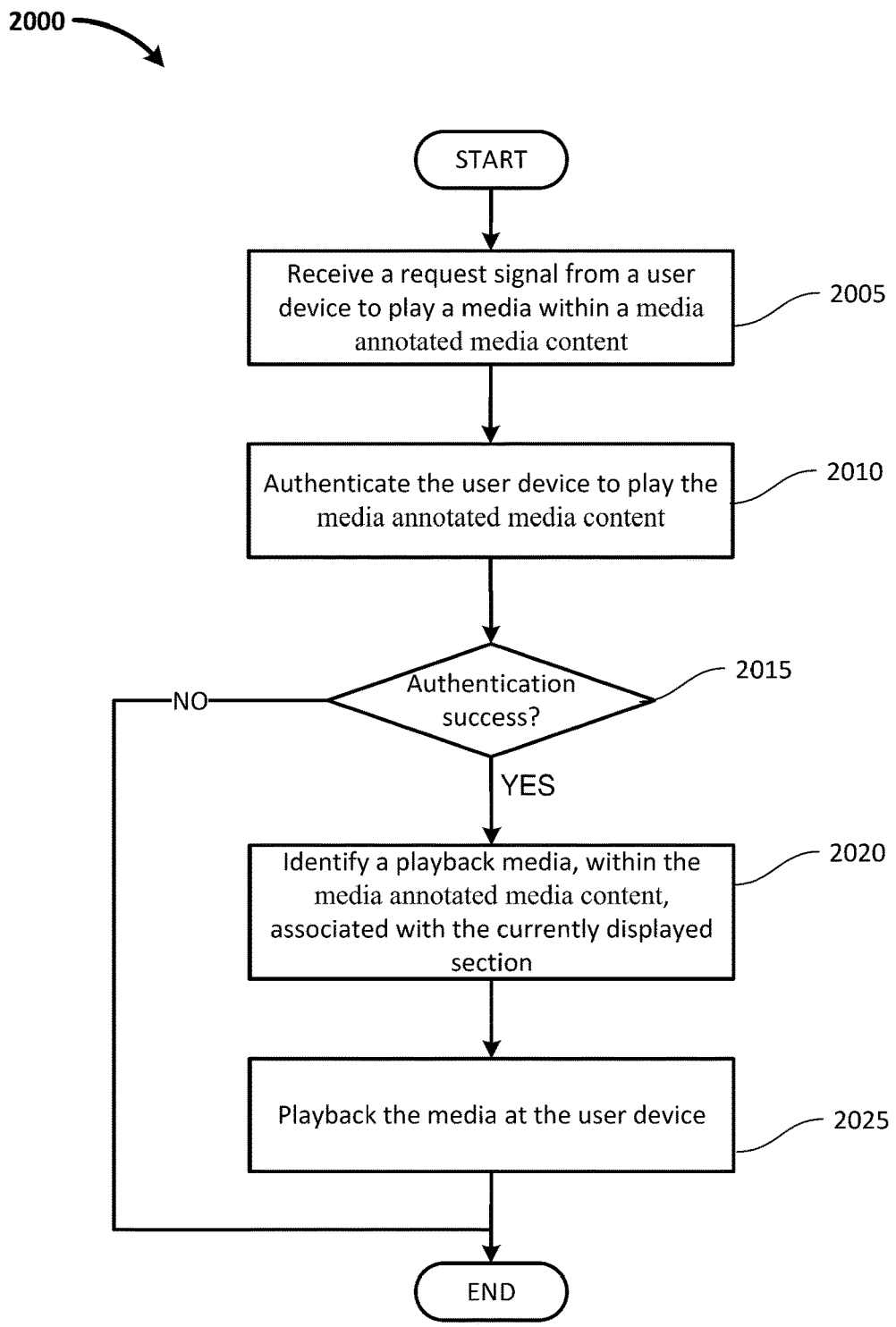
FIG. 20 is a flowchart illustrating an exemplary media playback method in a media annotated media content.

FIG. 20 is a flowchart illustrating an exemplary media playback method 2000 in a media annotated media content. For example, the HCDP 100 may execute the method 2000 to provide access to the generated media annotated medical content and playback of the media guidance for the patient 120. The method 2000 begins when a request signal is received from a user device to play a media within a media annotated media content in step 2005. Next, in step 2010, the user device to play the media annotated media content is authenticated. For example, the AAE 240 may perform the method 900 and/or the method 1000 to authenticate the device 116a.

In a decision point 2015, it is determined whether the authentication is successful. If the authentication is not successful, the method 2000 ends. If the authentication is successful, in step 2020, a section, a playback media, within the media annotated media content, associated with the currently displayed section is identified. For example, the display engine 258 may process the ".playback" file to identify the media associate with the section of the media annotated media content. Next, in step 2025, the media is played back at the user device. For example, a user may select the playback button 1805 to listen to a doctor's voice note regarding follow up appointments.

Although various embodiments have been described with reference to the figures, other embodiments are possible. For example, in some implementations, by way of example and not limitation, various components, systems, and/or engines may be embodied on one or more physical devices (e.g., servers, computing systems, networks). For example, in some implementations, separate servers and/or instances may be implemented in communication with one another. In some implementations, multiple components may, for example, be implemented in an integrated architecture. As an illustrative example, the DFGM 1305, external API 1330, and/or HCDP 100 as disclosed at least with reference to FIG. 13 may, for example, be implemented on one or more integrated and/or networked computing systems. As an illustrative example, the CAS 105, the data store 260, the medical devices 228, the FA server 220, the SCS 110, and/or the user devices 215 may, by way of example and not limitation, be implemented on one or more discrete, integrated, and/or networked computing systems.

In some implementations, the HCDP 100 may, for example, authorize access to and/or creation of live content. For example, media content may include a live video call and/or a live chat. For example, the HCDP 100 may be configured to provide a time-based access and/or creation token for joining, contributing to, and/or otherwise participating in a live digital media-based communication. In some implementations, by way of example and not limitation, the resulting media created may be recorded and stored in a digital object (e.g., created to store the media). The digital object may, for example, be associated with users and/or user devices credentialed by time-based tokens to join the live communication event. In some implementations, the digital object may, for example, be associated with a patient associated with the live media exchange (e.g., a patient discussed by two providers, a patient participating in the live media exchange). The digital object may, for example, be associated with an individual provider(s) and/or enterprise(s) involved in and/or otherwise associated with the patient and/or live media exchange. In some implementations, by way of example and not limitation, the live media exchange may be launched from a display on a user device such as the video call button 310 disclosed at least with reference to FIG. 3.

In some implementations, the HCDP 100 may include fully customizable workflows templates to allow teams to update and inform patients and relevant providers during a patient therapeutic journey. For example, upon updating that the patient is discharge from a hospital after a surgery, the workflow template may automatically notify a follow-up physician pre-authorized by the patient to contact the patient.

In some implementations, the HCDP 100 may connect to pharmacy systems. For example, the HCDP 100 may connect to the pharmacy systems via an Admission Discharge Transfer (ADT). For example, the patient may be notified from the HCDP 100 when medications are available. For example, the HCDP 100 may integrate with payment systems to collect payment from users.

Although an exemplary system has been described with reference to FIG. 1-2, other implementations may be deployed in other industrial, scientific, medical, commercial, and/or residential applications.

In some implementations, the CAS 105 and/or the SCS 110 may be implemented in a distributed computing network. For example, the distributed computing network may be implemented on a blockchain (e.g., an Ethereum virtual machine). For example, the distributed computing network may advantageously provide additional security to the HCDP 100.

In various embodiments, some bypass circuits implementations may be controlled in response to signals from analog or digital components, which may be discrete, integrated, or a combination of each. Some embodiments may include programmed, programmable devices, or some combination thereof (e.g., PLAs, PLDs, ASICs, microcontroller, microprocessor), and may include one or more data stores (e.g., cell, register, block, page) that provide single or multi-level digital data storage capability, and which may be volatile, non-volatile, or some combination thereof. Some control functions may be implemented in hardware, software, firmware, or a combination of any of them.

Computer program products may contain a set of instructions that, when executed by a processor device, cause the processor to perform prescribed functions. These functions may be performed in conjunction with controlled devices in operable communication with the processor. Computer program products, which may include software, may be stored in a data store tangibly embedded on a storage medium, such as an electronic, magnetic, or rotating storage device, and may be fixed or removable (e.g., hard disk, floppy disk, thumb drive, CD, DVD).

Although an example of a system, which may be portable, has been described with reference to the above figures, other implementations may be deployed in other processing applications, such as desktop and networked environments.

Temporary auxiliary energy inputs may be received, for example, from chargeable or single use batteries, which may enable use in portable or remote applications. Some embodiments may operate with other DC voltage sources, such as batteries, for example. Alternating current (AC) inputs, which may be provided, for example from a 50/60 Hz power port, or from a portable electric generator, may be received via a rectifier and appropriate scaling. Provision for AC (e.g., sine wave, square wave, triangular wave) inputs may include a line frequency transformer to provide voltage step-up, voltage step-down, and/or isolation.

Although particular features of an architecture have been described, other features may be incorporated to improve performance. For example, caching (e.g., L1, L2, . . . ) techniques may be used. Random access memory may be included, for example, to provide scratch pad memory and or to load executable code or parameter information stored for use during runtime operations. Other hardware and software may be provided to perform operations, such as network or other communications using one or more protocols, wireless (e.g., infrared) communications, stored operational energy and power supplies (e.g., batteries), switching and/or linear power supply circuits, software maintenance (e.g., self-test, upgrades), and the like. One or more communication interfaces may be provided in support of data storage and related operations.

Some systems may be implemented as a computer system that can be used with various implementations. For example, various implementations may include digital circuitry, analog circuitry, computer hardware, firmware, software, or combinations thereof. Apparatus can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Various embodiments can be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, which may include a single processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits).

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. Various embodiments may be implemented in a computer system that includes a graphical user interface and/or an Internet browser. To provide for interaction with a user, some implementations may be implemented on a computer having a display device, such as a CRT (cathode ray tube) or LCD (liquid crystal display) monitor for displaying information to the user, a keyboard, and a pointing device, such as a mouse or a trackball by which the user can provide input to the computer.

In various implementations, the system may communicate using suitable communication methods, equipment, and techniques. For example, the system may communicate with compatible devices (e.g., devices capable of transferring data to and/or from the system) using point-to-point communication in which a message is transported directly from the source to the receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, the computers and networks forming the Internet, or some combination thereof. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Firewire, ATA/IDE, RS-232, RS-422, RS-485, 802.11 a/b/g, Wi-Fi, Ethernet, IrDA, FDDI (fiber distributed data interface), token-ring networks, multiplexing techniques based on frequency, time, or code division, or some combination thereof. Some implementations may optionally incorporate features such as error checking and correction (ECC) for data integrity, or security measures, such as encryption (e.g., WEP) and password protection.

In various embodiments, the computer system may include Internet of Things (IoT) devices. IoT devices may include objects embedded with electronics, software, sensors, actuators, and network connectivity which enable these objects to collect and exchange data. IoT devices may be in-use with wired or wireless devices by sending data through an interface to another device. IoT devices may collect useful data and then autonomously flow the data between other devices.

Various examples of modules may be implemented using circuitry, including various electronic hardware. By way of example and not limitation, the hardware may include transistors, resistors, capacitors, switches, integrated circuits, other modules, or some combination thereof. In various examples, the modules may include analog logic, digital logic, discrete components, traces and/or memory circuits fabricated on a silicon substrate including various integrated circuits (e.g., FPGAs, ASICs), or some combination thereof. In some embodiments, the module(s) may involve execution of preprogrammed instructions, software executed by a processor, or some combination thereof. For example, various modules may involve both hardware and software.

In an illustrative aspect, a computer program product may include a program of instructions tangibly embodied on a non-transitory computer readable medium wherein, when the instructions are executed on a processor, the processor causes operations to be performed to automatically provide transient user credentialing for interaction with patient health data based on predetermined associations with a user, a patient associated with the patient health data, and a patient health data originator. The operations may include receive, from a device of a requestor, a signal corresponding to a request for access to health records of a patient from a first data store. The operations may include, in response to receiving the signal, determine a plurality of predetermined digital records stored in the first data store based on a predetermined association with the patient;

retrieve, from at least a second data store, a patient relation object and a patient identification object associated with the patient. The operations may include determine, based on the patient relation object, whether a predetermined association between the requestor and the patient exists and meets a first predetermined access criterion. The operations may include, upon determining that the predetermined association is determined to meet the first predetermined access criterion, then, determine, based on the patient relation object, a predetermined role for the requestor with relation to the patient. The operations may include generate, in a memory device, an authenticated access token data structure configured to receive time-limited access tokens corresponding to selected digital records with authenticated access selected from the plurality of predetermined digital records associated with the patient. The operations may include, for each of the plurality of predetermined digital records, perform access selection operations. The access selection operations may include determine, based on the predetermined role and on metadata associated with a currently selected predetermined digital record of the plurality of predetermined digital records, whether the predetermined role meets a second predetermined access criterion. The access selection operations may include determine, based on the patient identification object and a creator identification object associated with the currently selected predetermined digital record, whether a predetermined association between the requestor and a creator of the currently selected predetermined digital record exists and meets a third predetermined access criterion. The access selection operations may include, upon determining that the first predetermined access criterion, the second predetermined access criterion, and the third predetermined access criterion are satisfied, then generate a time-limited access token for the currently selected predetermined digital record, wherein the time-limited access token comprises a uniform resource identifier, having a time sensitive unique access code, to a playback address associated with a corresponding digital record. The access selection operations may include insert the time-limited access token to the authenticated access token data structure. The operations may include generate a human-readable display comprising a human-readable indicium for each of at least some of the generated time-limited access tokens. The operations may include transmit, to the device of the requestor, the time-limited access tokens stored within the authenticated access token data structure such that the requestor is provided temporary streaming access to authenticated digital records of the plurality of predetermined digital records based on the first predetermined access criterion, the second predetermined access criterion, and the third predetermined access criterion.

The operations may include generate a time-limited creation token providing access to associate digital content from the requestor with the patient. The time-limited creation token may be generated based on: a predetermined association of the requestor with the patient, and a predetermined role of the requestor with relation to the patient.

The may include a medical device automatically saving digital content to the first data store.

Each time-limited access token may be further generated based on a predetermined association between the requestor and an organization associated with the patient.

The first predetermined access criterion may include one or more authorized entities, preselected by the patient, having a predetermined access credential to at least some of the patient health data.

The operations may include receive the time-limited access token for accessing a digital content associated with the time-limited access token. The operations may include authenticate the time-limited access token. the operations may include request the requestor to complete a two-factor authorization operation.

The two-factor authorization operation may include: receive a signal representing a date of birth; and, validate that the date of birth received in the signal matches a predetermined date of birth associated with the patient.

The time-limited access token may, for example, be valid for less than 48 hours. The time-limited access token may, for example, be valid for less than 30 minutes. The time-limited access token may, for example, be valid for less than 15 minutes. The time-limited access token may, for example, be valid for less than 5 minutes.

The time-limited creation token may, for example, be valid for less than 48 hours. The time-limited creation token may, for example, be valid for less than 30 minutes. The time-limited creation token may, for example, be valid for less than 15 minutes. The time-limited creation token may, for example, be valid for less than 5 minutes.

In an illustrative aspect, a computer program product may include a program of instructions tangibly embodied on a non-transitory computer readable medium wherein, when the instructions are executed on a processor, the processor causes operations to be performed to automatically provide transient user credentialing for interaction with patient health data based on predetermined associations with a user, a patient associated with the patient health data, and a patient health data originator. The operations may include receive, from a device of a requestor, a signal corresponding to a request for access to health records of a patient from a first data store. The operations may include, in response to receiving the signal, determine a plurality of predetermined digital records stored in the first data store based on a predetermined association with the patient;

retrieve, from at least a second data store, a patient relation object and a patient identification object associated with the patient. The operations may include determine, based on the patient relation object, whether a predetermined association between the requestor and the patient exists and meets a first predetermined access criterion. The operations may include, upon determining that the predetermined association is determined to meet the first predetermined access criterion, then, determine, based on the patient relation object, a predetermined role for the requestor with relation to the patient. The operations may include generate, in a memory device, an authenticated access token data structure configured to receive time-limited access tokens corresponding to selected digital records with authenticated access selected from the plurality of predetermined digital records associated with the patient. The operations may include, for each of the plurality of predetermined digital records. The access selection operations may include determine, based on the predetermined role and on metadata associated with a currently selected predetermined digital record of the plurality of predetermined digital records, whether the predetermined role meets a second predetermined access criterion. The access selection operations may include determine, based on the patient identification object and a creator identification object associated with the currently selected predetermined digital record, whether a predetermined association between the requestor and a creator of the currently selected predetermined digital record exists and meets a third predetermined access criterion. The access selection operations may include, upon determining that the first predetermined access criterion, the second predetermined access criterion, and the third predetermined access criterion are satisfied, then generate a time-limited access token for the currently selected predetermined digital record. The access selection operations may include insert the time-limited access token to the authenticated access token data structure. The operations may include transmit, to the device of the requestor, the time-limited access tokens stored within the authenticated access token data structure such that the requestor is provided temporary streaming access to authenticated digital records of the plurality of predetermined digital records based on the first predetermined access criterion, the second predetermined access criterion, and the third predetermined access criterion.

The operations may include: generate a time-limited creation token providing access to associate digital content from the requestor with the patient. The time-limited creation token may be generated based on: a predetermined association of the requestor with the patient, and a predetermined role of the requestor with relation to the patient. The requestor may include a medical device automatically saving digital content to the first data store.

Each time-limited access token may be further generated based on a predetermined association between the requestor and an organization associated with the patient.

The first predetermined access criterion may include one or more authorized entities, preselected by the patient, having a predetermined access credential to at least some of the patient health data.

The operations may include receive the time-limited access token for accessing a digital content associated with the time-limited access token. The operations may include authenticate the time-limited access token. The operations may include request the requestor to complete a two-factor authorization operation. The operations may include transmit a link to a user device of the requestor to transiently display the digital content associated with the time-limited access token. The two-factor authorization operation may include receive a signal representing a date of birth; and, validate the date of birth matches a date of birth associated with the patient.

The time-limited access token may include a uniform resource identifier, having a time sensitive unique access code, to a playback address associated with a corresponding digital record.

The operations may include generate a human-readable display including a human-readable indicium for each of at least some of the generated time-limited access tokens.

The time-limited access token may be valid, for example, for less than 48 hours.

The operations may include receive a data stream corresponding to patient instructions. The operations may include generate, from the data stream, a plurality of visual displays comprising visual indicia representing the patient instructions. The operations may include provide, in a series of display events, the plurality of visual displays to an authorized content creation user, each of the plurality of visual displays being presented with a corresponding visual indicia prompting the authorized content creation user to record a media file associated with a currently presented display of the plurality of visual displays. The operations may include, when a media file is recorded by the authorized content creation user, associate the media file with the currently presented display. The operations may include save, in a predetermined file format, an association between each of the plurality of visual displays for which at least one media file was recorded and the corresponding at least one media file.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A computer program product comprising:
a program of instructions tangibly embodied on a non-transitory computer readable medium wherein, when the instructions are executed on a processor, the processor causes operations to be performed to automatically provide transient user credentialing for access of secure media content based on predetermined associations with a user, a target entity associated with the secure media content, and a content contributor, the operations comprising:
   receive, from a device of a requestor, a signal corresponding to a request for accessing secure media content of a target entity from a first data store;
   in response to receiving the signal, determine a plurality of predetermined digital records stored in the first data store based on a predetermined association with the target entity;
   retrieve, from at least a second data store, an audience relation object and an audience identification object associated with the target entity;
   determine, based on the audience relation object, whether a first predetermined association between the requestor and the target entity exists and meets a first predetermined access criterion;
   upon determining that the first predetermined association is determined to meet the first predetermined access criterion, then, determine, based on the audience relation object, a predetermined role for the requestor with relation to the target entity;
   generate, in a memory device, an authenticated access token data structure configured to receive time-limited access tokens corresponding to selected digital records with authenticated access selected from the plurality of predetermined digital records associated with the target entity;
   perform access selection operations for each of the plurality of predetermined digital records determined in response to the receiving signal, the access selection operations comprising:
      determine, based on the predetermined role and on metadata associated with a currently selected predetermined digital record selected from the plurality of predetermined digital records, whether the predetermined role meets a second predetermined access criterion;

determine, based on the audience identification object and a creator identification object associated with the currently selected predetermined digital record, whether a second predetermined association between the requestor and a creator of the currently selected predetermined digital record exists and meets a third predetermined access criterion; and, upon determining that the first predetermined access criterion, the second predetermined access criterion, and the third predetermined access criterion are satisfied, then generate a time-limited access token for the currently selected predetermined digital record; and, transmit, to the device of the requestor, a plurality of the time-limited access tokens generated by the access selection operations and stored within the authenticated access token data structure, such that the requestor is provided temporary streaming access to the secure media content corresponding authenticated digital records of the plurality of predetermined digital records based on the first predetermined access criterion, the second predetermined access criterion, and the third predetermined access criterion.

2. The computer program product of claim 1, wherein: the target entity comprises a patient;
the secure media content comprises patient health data; the audience relation object comprises a patent relation object; and,
the audience identification object comprises a patent identification object.

3. The computer program product of claim 1, wherein the operations further comprise:
generate a time-limited creation token providing access to associate digital content from the requestor with the target entity,
wherein the time-limited creation token is generated based on:
the first predetermined association of the requestor with the target entity, and
the predetermined role of the requestor with relation to the target entity.

4. The computer program product of claim 3, wherein the requestor comprises a mobile device automatically saving the secure media content to the first data store.

5. The computer program product of claim 4, wherein the mobile device comprises a camera.

6. The computer program product of claim 1, wherein each of the time-limited access tokens is further generated based on a third predetermined association between the requestor and an organization associated with the target entity.

7. The computer program product of claim 1, wherein the first predetermined access criterion comprises one or more authorized entities, preselected by the target entity, having a predetermined access credential to at least some of the secure media content.

8. The computer program product of claim 1, wherein the operations further comprise:
receive the time-limited access token for accessing a digital content associated with the time-limited access token;
authenticate the time-limited access token;
request the requestor to complete a two-factor authorization operation; and,
transmit a link to a user device of the requestor to transiently display the digital content associated with the time-limited access token.

9. The computer program product of claim 8, wherein the two-factor authorization operation comprises:
receive a signal representing a date of birth; and,
validate the date of birth matches a date of birth associated with the target entity.

10. The computer program product of claim 1, wherein the time-limited access token comprises a uniform resource identifier, having a time sensitive unique access code, to a playback address associated with a corresponding digital record.

11. The computer program product of claim 1, wherein the operations further comprise:
generate a human-readable display comprising a human-readable indicium for each of at least some of the generated time-limited access tokens.

12. The computer program product of claim 11, wherein the time-limited access token is valid for less than 48 hours.

13. The computer program product of claim 11, wherein the operations further comprise:
receive a data stream corresponding to guidance for the target entity;
generate, from the data stream, a plurality of visual displays comprising visual indicia representing the guidance;
provide, in a series of display events, the plurality of visual displays to an authorized content creation user, each of the plurality of visual displays being presented with a corresponding visual indicia prompting the authorized content creation user to record a media file associated with a currently presented display of the plurality of visual displays;
when the media file is recorded by the authorized content creation user, associate the media file with the currently presented display; and,
save, in a predetermined file format, an association between each of the plurality of visual displays for which at least one media file was recorded and the corresponding at least one media file.

14. The computer program product of claim 1, wherein the secure media content comprises a customizable workflows template.

15. The computer program product of claim 1, wherein the secure media content comprises a data structure of personal information associated with the target entity.

16. The computer program product of claim 1, wherein, when the signal corresponding to the request for accessing the secure media content of the target entity is initiated by a conference call, the operations further comprise:
upon determining that a connection is successful, temporarily generate the first predetermined association between the requestor and the target entity, and the predetermined role of the requestor, such that the requestor gains access to at least some secure media content of the target entity.

17. The computer program product of claim 1, wherein the operations further comprise:
receive an activation signal from the requestor;
generate a list of authenticated target entity, wherein the list of authenticated target entity comprises at least one target entity who meets the first predetermined access criterion; and, transmit the list of authenticated target entity to be displayed at a user device of the requestor.

18. The computer program product of claim 1, wherein the operations further comprise:
    generate a role-specific display of the secure media content based on the predetermined role of the requestor.

19. The computer program product of claim 1, wherein the time-limited access token comprises a sharable transient access code, wherein the user accessing the secure media content associated with the sharable transient access code is not required to be authenticated with the first predetermined access criterion, the second predetermined access criterion, and the third predetermined access criterion.

20. The computer program product of claim 19, wherein the sharable transient access code comprises a quick response code.

* * * * *